(12) United States Patent
Deschenes

(10) Patent No.: US 7,625,863 B2
(45) Date of Patent: Dec. 1, 2009

(54) TREATMENT OF PATIENTS WITH DYSFUNCTIONAL CARDIAC SODIUM CHANNELS

(75) Inventor: Isabelle Deschenes, North Ridgeville, OH (US)

(73) Assignee: The MetroHealth System, Cleveland, OH (US)

( * ) Notice: Subject to any disclaimer, the term of this patent is extended or adjusted under 35 U.S.C. 154(b) by 0 days.

(21) Appl. No.: 11/927,398

(22) Filed: Oct. 29, 2007

(65) Prior Publication Data

US 2008/0214457 A1 Sep. 4, 2008

Related U.S. Application Data

(60) Provisional application No. 60/854,968, filed on Oct. 27, 2006.

(51) Int. Cl.
*A61K 38/04* (2006.01)
*A61K 38/16* (2006.01)
*C07K 11/00* (2006.01)
*C07K 14/00* (2006.01)

(52) U.S. Cl. ............................. 514/2; 514/12; 530/300

(58) Field of Classification Search ....................... None
See application file for complete search history.

(56) References Cited

OTHER PUBLICATIONS

Wells, J.A. (1990). Additivity of mutational effects in proteins. Biochemistry. 29(37):8509-8517.*

Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*

Skolnick et al. (2000). From genes to protein structure and function: novel applications of computational approaches in the genomic era. Trends in Biotechnology. 18:34-39.*

Aleong, R., et al. "The Cardiac Sodium Channel H558R Variant Improves Survival in Heart Failure", Heart Rhythm, (2005) 2: 5104-05.

Baroudi, G., et al., "Expression and Intracellular Localization of an SCN5A Double Mutant R1232W/T1620M Implicated in Brugada Syndrome" Circ Res. (2002) 90:E11-E16.

Cormet-Boyaka, E., et al., "Rescuing cystic fibrosis transmembrane conductance regulator (CFTR)-processing mutants by transcomplementation," Proc. Natl. Acad. Sci. USA (2004), 101:8221-6.

Deschenes, I., et al., "Electrophysiological characterization of SCN5A mutations causing long QT (E1784K) and Brugada (R1512W and R1432G) Syndromes", Cardiovasc Res. (2000) 46:55-65.

Gouas L., et al., for the D.E.S.I.R. Study Group. Association of KCNQ1, KCNE1, KCNH2 and SCN5A polymorphisms with QTc interval length in a healthy population, Eur J Hum Genet. (2005) 13:1213-1222.

Itoh et al., "Genomic organization and mutational analysis of HERG, a gene responsible for familial long QT syndrome", Hum. Genet, 102, pp. 435-439 (1998).

Jenke et al., "C-terminal domains implicated in the functional surface expression of potassium channels", EMBO J. 22, pp. 395-403 (2003).

Kanki, H., et al., "A structural requirement for processing the cardiac K+ channel KCNQ1," J. Biol. Chem. (2004) 279:33976-83.

Kupershmidt, S., et al., "Defective human Ether-a-go-go-related gene trafficking linked to an endoplasmic reticulum retention signal in the C terminus," J. Biol. Chem. (2002) 277:27442-8.

Niu, D.M., et al., "A common SCN5A polymorphism attenuates a severe cardiac phenotype caused by a nonsense SCN5A mutation in a Chinese family with an inherited cardiac conduction defect," J. Med. Genet. (2006) 43:817-21.

Owsianik, G., et al., "Rescue of functional DeltaF508-CFTR channels by co-expression with trancated CFTR constructs in COS-1 cells," FEBS Lett. (2003) 554:173-8.

Palomeque, J., et al., "Efficiency of eight different AAV serotypes in transducing rat myocardium in vivo," Gene Ther. (2007) 14:989-97.

Ye, B., et al., "A common human SCN5A polymmorphism modifies expression of an arrhythmia causing mutation" Physiol Genomics. (2003) 12:187-195.

Poelzing et al. "SCN5A polymorphism restores trafficking of a Brugada syndrome mutation on a separate gene", (2006) Circulation 114:368-376.

Priori et al., "Molecular Underpinning of "Good Luck"" Circulation (2002) 105:1342-1347.

Shinlapawittayatorn, K., et al., "SCN5A Polymophism Modifies Gating Kinetics in a LQT3 Mutation: an Alternative Treatment for Mutated Sodium Channels?" MetroHealth Poster, CVS Festival, presention Sep. 27, 2007.

Takehara et al., "A Cardiac sodium channel mutation identified in Brugada syndrome associated with atrial standstill", J. Intern. Med, 255, pp. 137-142 (2004).

Tan, HL, Sodium Channel Variants in Heart Disease: Expanding Horizons, J Cardiovasc. Electrophysiol. 17 (Suppl. 1) S151-157 (2006).

Vatta et al., "Novel mutations in domain I of SCN5A cause Brugada syndrome", Mol. Genet. Metab, 75, pp. 317-324 (2002).

Viswanathan PC, et al., "A common SCN5A polymorphism modulates the biophysical effects of an SCN5A mutation," J. Clin Invest. (2003) 111:341-346.

(Continued)

*Primary Examiner*—Christine J Saoud
*Assistant Examiner*—Jon M Lockard
(74) *Attorney, Agent, or Firm*—Calfee Halter & Griswold LLP

(57) ABSTRACT

Isolated peptides and polynucleotides are provided that can be used to treat a subject that has a genetic predisposition to, or has been diagnosed as having, a cardiac disorder related to dysfunctional sodium channels. Also provided are methods of treatment, as well as methods of predicting the occurrence of a cardiac event or the severity or prognosis of cardiac symptoms, in a subject that has either been diagnosed as having, or is suspected of developing, a sodium channel related cardiac disorder, by testing the subject for the presence of H558R-polymorphism on the subject's SCN5A gene.

10 Claims, 14 Drawing Sheets

OTHER PUBLICATIONS

Weiss et al., "Clinical and molecular heterogeneity in the Brugada syndrome: a novel gene locus on chromosome 3", Circulation, 105, pp. 707-713 (2002).

Yang, P., et al., "Allelic variants in long-QT disease genes in patients with drug-associated torsades de pointes," Circulation (2002) 105:1943-1946.

PubMed Accession No. NM 198056.2 (gi 124518659), Feb. 7, 2007.

PubMed Accession No. NM 198056 (gi37622906), Mar. 4, 2006.

Pitzalis et al., "QT-interval prolongation in right precordial leads: an additional electrocardiographic hallmark of Brugada syndrome" J. Am Coll Cardiol. (2003) 42:1632-7.

Dudash et al., "Gene Therapy using Fragments of the SCN5A H558R Polymorphism Restores Function of a Brugada Syndrome Mutation", Case Western Reserve University, Cleveland, Ohio, published on line Oct. 31, 2006.

Shinlapawittayatorn et al., "3087-Pos/B390. SCN5A Polymorphism Decreases Arrhythmogenic Events in a FAmily Carrying a LQT3 Mutation", Case Western Reserve University, Cleveland, Ohio, Jan. 2008.

* cited by examiner

SEQUENCE LISTING

<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Glu Ser His Arg Thr Ser Leu Leu Val
1               5                   10

<210> SEQ ID NO 2
<211> LENGTH: 100
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Leu Ser Leu Thr Arg Gly Leu Ser Arg Thr Ser Met Lys Pro Arg
1               5                   10                  15

Ser Ser Arg Gly Ser Ile Phe Thr Phe Arg Arg Asp Leu Gly Ser
            20                  25                  30

Glu Ala Asp Phe Ala Asp Asp Glu Asn Ser Thr Ala Gly Glu Ser Glu
35                  40                  45

Ser His Arg Thr Ser Leu Leu Val Pro Trp Pro Leu Arg Arg Thr Ser
50                  55                  60

Ala Gln Gly Gln Pro Ser Pro Gly Thr Ser Ala Pro Gly His Ala Leu
65                  70                  75                  80

His Gly Lys Lys Asn Ser Thr Val Asp Cys Asn Gly Val Val Ser Leu
85                  90                  95

Leu Gly Ala Gly
100

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Ser Thr Ala Gly Glu Ser Glu Ser His Arg Thr Ser Leu Leu Val
1               5                   10                  15

Pro Trp Pro Leu
20

<210> SEQ ID NO 4
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ser Glu Ala Asp Phe Ala Asp Asp Glu Asn Ser Thr Ala Gly Glu

-continued

```
1               5               10              15
Ser Glu Ser His Arg Thr Ser Leu Leu Val Pro Trp Pro Leu Arg Arg
20              25              30
Thr Ser Ala Gln Gly Gln Pro Ser
35              40

<210> SEQ ID NO 5
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
catctcagcc tcacccgtgg cctcagcagg acttctatga agccacgttc cagccgcggg    60
agcattttca cctttcgcag gcgagacctg ggttctgaag cagattttgc agatgatgaa   120
aacagcacag cggggagag cgagagccac cgcacatcac tgctggtgcc ctggccctg     180 cgccggacca gtgcccaggg acagcccagt cccggaacct cggctcctgg ccacgccctc   240
catggcaaaa agaacagcac tgtggactgc aatggggtgg tctcattact ggggcaggc   300

<210> SEQ ID NO 6
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
ggttctgaag cagattttgc agatgatgaa aacagcacag cggggagag cgagagccac     60 cgcacatcac tgctggtgcc ctggccctg cgccggacca gtgcccaggg acagcccagt    120

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
aacagcacag cggggagag cgagagccac cgcacatcac tgctggtgcc ctggccctg      60

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gagagccacc gcacatcact gctggtgccc                                     30

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
-continued

<400> SEQUENCE: 9

Glu Ser His Arg Thr Ser Leu Leu Val Pro
1               5                   10

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Ser Thr Ala Arg Glu Ser Glu Ser His His Thr Ser Leu Leu Val
1               5                   10                  15

Pro Trp Pro Leu
        20
```

TREATMENT OF PATIENTS WITH DYSFUNCTIONAL CARDIAC SODIUM CHANNELS

RELATED APPLICATIONS

This application claims priority to U.S. Provisional Application Ser. No. 60/854,968; filed Oct. 27, 2006, the entire contents of which is incorporated herein by reference.

BACKGROUND

The cardiac sodium (Na) channel controls cardiac excitability and the velocity of impulse propagation as it initiates the cardiac action potential (AP). Accordingly, derangements of cardiac sodium channel function affect excitability in ways that may culminate in cardiac arrhythmias. Previous studies have shown many inherited arrhythmia syndromes to be caused by sodium channel dysfunction secondary to mutations in SCN5A, the gene that encodes the pore-forming α-subunit of the cardiac sodium channel (hNav1.5) in the cell membranes of the muscle cells of the heart (the myocytes).

Two examples of inherited arrhythmias are Brugada and long QT-3 syndromes, two allelic diseases caused by different mutations in SCN5A gene inherited by an autosomal dominant pattern with variable penetrance. Loss-of-function mutations in this gene lead to a loss of whole cell sodium current.

Both of these syndromes are ion channel diseases of the heart that manifest on surface electrocardiogram (ECG) by ST-segment elevation in the right precordial leads and prolonged QT(c) interval, respectively, with predilection for polymorphic ventricular tachycardia and sudden death, which may be the first manifestation of the disease.

Brugada syndrome (BrS), also known as Sudden Unexpected Death Syndrome (SUDS), is an autosomal dominant disease with an increased risk of sudden cardiac death. It usually manifests during adulthood with male preponderance. This syndrome is also characterized by a high occurrence of incomplete penetrance, so that many patients with a BrS causing mutation never develop symptoms of the disease. Thus, there is great difficulty and debate over determining which patients are likely to develop a life threatening arrhythmia and who may need preventive therapy.

The cause of death in Brugada syndrome is ventricular fibrillation. The episodes of syncope (fainting) and sudden death (aborted or not) are caused by fast polymorphic ventricular tachycardias or ventricular fibrillation. These arrhythmias appear with no warning. The current treatment options for Brugada Syndrome include implantable cardioverter-defibrillator (ICD) and drug therapy. The ICD continuously monitors the heart rhythm and will defibrillate an individual if ventricular fibrillation is noted and is the only known method for preventing sudden cardiac death. However, ICD's are costly, can inappropriately shock their recipients, and are known to cause complications especially at the lead site. Furthermore, an ICD is not able to prevent future arrhythmias since it does not treat the channel dysfunction that is the underlying source of the arrhythmia. Pharmacological treatments for BrS are also being explored. Studies show that delivery of the sodium channel blocker, quinidine, reduces the inducibility of arrhythmias in electrophysiological studies, but is also associated with side effects that caused some patients to stop the therapy.

In congenital long QT syndrome, the electrocardiogram QT interval is prolonged due to dysfunctional ventricular repolarization. LQT syndrome is associated with syncope and sudden death and causes 3000 to 4000 sudden deaths in children and young adults each year in the US alone. Variant 3 (LQT-3) is associated with mutations in SCN5A. Arrhythmias in LQT-3 mutation carriers are more likely to occur at rest, when heart rate is slow. Congenital long QT syndrome, a rare disease in which the QT interval of the electrocardiogram is prolonged due to dysfunctional ventricular repolarization, Long QT3 syndrome usually manifests in teenage years, although it can also manifest in adulthood.

In symptomatic patients of long QT-3 syndrome in whom the torsade de pointes is bradycardia-dependent or pause-dependent, a pacemaker could be used to avoid bradycardia and pauses and an implantable cardioverter defibrillator is indicated where arrhythmia is not controlled with pacemaker and beta-blockade. These methods, however, have the shortcomings discussed above.

Recent studies indicate that sodium channel dysfunction may also be involved in structural and acquired cardiac defects. (Tan, H L, 2006, *J Cardiovac Electrophysiol* 17:S151-S157). A study of congestive heart failure found that enhanced sodium currents may be one of the underlying causes of arrhythmia in congestive heart failure.

Heart failure is often defined as the inability of the heart to deliver a supply of oxygenated blood sufficient to meet the metabolic needs of peripheral tissues, both at rest and during exercise. See generally, Hutter, Jr., "Congestive Heart Failure", in Scientific American: Medicine, Volume 1 (1:II), eds. Dale and Federman (Scientific American, Inc. 1994).

The American Heart Association (AHA) 2006 update on heart disease reported that 5 million Americans are believed to have symptomatic heart failure (HF), and 550,000 patients are newly diagnosed each year. The estimated direct and indirect cost of HF in the United States (U.S.) for 2006 will be ~$29.6 billion. Heart failure is a disabling chronic disease and the most frequent discharge diagnosis for hospitalization among older adults. Despite the significant resources expended on the treatment of this disease, outcomes remain poor. The five-year survival for individuals diagnosed with heart failure is less than 50%, and in end-stage heart failure, the one-year survival may be as low as 25% regardless of medical therapy. One major cause of death in heart failure patients is cardiac arrhythmias.

Despite continuous improvements, the treatment of heart failure is at this time unsatisfactory. Although the foundation of this disease is represented by the decrease in cardiac contractility, only two classes of drugs are approved for use to increase cardiac force (i.e. positive inotropes), cardiac glycosides (like digoxin) and beta-adrenergic agonists (like dobutamine, amrinone or milrinone). Importantly, despite an effective relief of symptoms, the use of these agents has been associated with no change (digoxin) or an increase (beta-adrenergic agonists) in mortality.

Other classes of agents used in heart failure exert their beneficial effects by preventing the long term cardiac remodeling of ion channels seen in heart failure that results in high risks of arrhythmias or by interfering with renal and vascular contributory mechanisms, both of which suffer from negative effects on both physician confidence and patient compliance. The need for new, effective treatments is, therefore, evident.

In sum, there remains a need to develop effective treatments for cardiac arrhythmias caused by ion channel disorders that avoid the complications of ICD's and drug therapy, but also address the underlying causes of the conditions that increase the risk for such arrhythmias.

SUMMARY

Disclosed herein are isolated peptides having a sequence that is from 10 to 100 amino acids in length, wherein the peptides comprise the sequence SESHRTSLLV, SEQ ID NO: 1. and are at least 90% identical to all or a portion of SEQ ID NO. 2.

In one embodiment, the peptides have a sequence that is 98% identical to all or a portion of SEQ ID No. 2.

In other embodiments, the peptides have the sequence SEQ ID NO. 2, SEQ ID NO. 4, SEQ ID NO. 3, SEQ ID NO. 1, or SEQ ID NO: 9.

Also disclosed are methods for treating a subject that has a genetic predisposition to, or has been diagnosed as having, a cardiac disorder related to dysfunctional sodium channels. The methods include administering to the subject a therapeutically effective amount of one or more peptides disclosed herein.

Also disclosed are isolated polynucleotides that encode peptides having a sequence that is from 10 to 100 amino acids in length, wherein the encoded peptides include the sequence SESHRTSLLV, SEQ ID NO: 1. and are at least 90% identical to all or a portion of SEQ ID NO. 2.

In one embodiment, the isolated polynucleotides encode a peptide that has a sequence that is 98% identical to all or a portion of SEQ ID No. 2.

In other embodiments, the isolated polynucleotide encodes a peptide that has the sequence SEQ ID NO. 2, SEQ ID NO. 4, SEQ ID NO. 3, SEQ ID NO. 1 or SEQ ID NO. 9.

Also disclosed are gene therapy methods for treating a subject that has a genetic predisposition to, or has been diagnosed as having, a cardiac disorder related to dysfunctional sodium channels by administering to the subject a therapeutically effective amount of a polynucleotide disclosed herein.

In one embodiment of the gene therapy method, the polynucleotide is operably linked to a tissue specific promoter that promotes expression of the polynucleotide in myocytes of the subject.

Also disclosed are expression vectors that include the polynucleotides disclosed herein.

In some embodiments, the methods of treatment are contemplated for subjects who have a genetic predisposition to, or have been diagnosed as having: Brugada's syndrome, long QT syndrome, or heart failure.

Also disclosed are methods for predicting the occurrence of a cardiac event in a subject, wherein the subject has either (a) been diagnosed as having a cardiac disorder, (b) is suspected of developing a cardiac disorder, comprising testing the subject for the presence of H558R-polymorphism on the subject's SCN5A gene, wherein the presence of the H558R-polymorphism is predictive that the cardiac event is less likely to occur.

Also disclosed are methods for predicting the severity or prognosis of cardiac symptoms in a subject, wherein the subject has either (a) been diagnosed as having a cardiac disorder, (b) is suspected of developing a cardiac disorder. The method includes testing the subject for the presence of H558R-polymorphism on the subject's SCN5A gene, wherein the presence of the H558R-polymorphism is predictive of less severe cardiac symptoms or better prognosis in the subject. In one example of this method, the prediction of better prognosis in the subject includes prediction of response to therapy.

In one embodiment of the predictive methods described above, the cardiac disorder is due to dysfunctional sodium channels in the heart.

In other embodiments, the subject is diagnosed as having, or is suspected of developing, Brugada syndrome, Long QT3 syndrome, or heart failure.

In some examples, the cardiac event is cardiac arrhythmia. In other examples, the cardiac event is cardiac arrest.

In some embodiment, the subject has a disease-causing mutation on one allele of the SCN5A gene and the H558R-polymorphism is present on another allele of the SCN5A gene. In one example, the disease causing mutation is R282H-SCN5A.

In other embodiments, the subject has a R282H-SCN5A mutation on one allele of the SCN5A gene and the H558R-polymorphism is present, and the cardiac event is cardiac arrhythmia.

In other embodiments, the subject has a SCN5A-P2006A mutation on one allele of the SCN5A gene and the H558R-polymorphism is present, and the cardiac event is cardiac arrhythmia.

DETAILED DESCRIPTION

Figure 1:
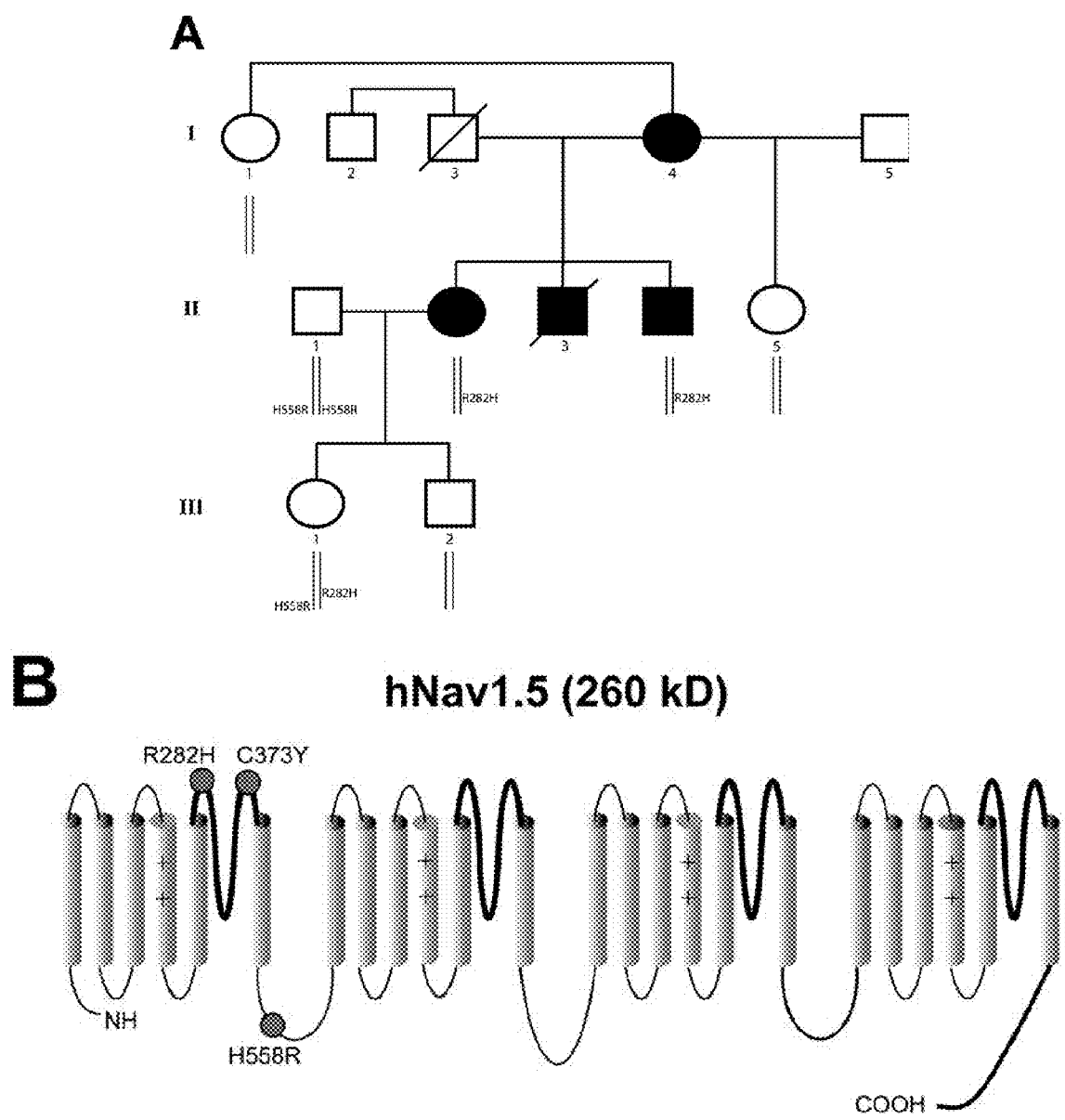
FIG. 1. A, Pedigree of a family with BrS. The solid symbols represent the individuals clinically identified with the disease. Individual III-1 is asymptomatic and does not show the typical BrS ECG pattern despite having the R282H-SCN5A mutation. That individual also has an H558R-SCN5A polymorphism on a second allele. B, Diagram of hNav1.5. Circles represent amino acid residues where mutations and/or polymorphisms occur that are subsequently characterized in this report.

The present invention will now be described with occasional reference to some specific embodiments disclosed herein. This invention may, however, be embodied in different forms and should not be construed as limited to the embodiments set forth herein. Rather, these embodiments are provided so that this disclosure will be thorough and complete, and will fully convey the scope to those skilled in the art.

Unless otherwise defined, all technical and scientific terms used herein have the same meaning as commonly understood by one of ordinary skill in the art to which this invention belongs. The terminology used in the description herein is for describing particular embodiments only and is not intended to be limiting. As used in the description and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope are approximations, the numerical values set forth in the specific examples are reported as precisely as possible. Any numerical values, however, inherently contain certain errors necessarily resulting from error found in their respective measurements.

Provided herein are isolated peptides, isolated polynucleotides, methods of using such peptides and polynucleotides for treatment of subjects who have, or are at risk of developing, a cardiac disorder. Also included are methods of predicting the likelihood of developing symptoms, prognosis, severity, response to therapy, and outcome of subjects with a cardiac disorder related to dysfunctional protein channels.

Accordingly, provided herein are one or more isolated peptides having a sequence that is from 10 to 100 amino acids in length, where the peptide includes the sequence SESHRTSLLV, SEQ ID NO: 1. and is at least 90% identical to all or a portion of SEQ ID NO. 2.

Such a peptide can have sequence identity of 90%, 91%, 92%, 93%, 94%, 95%, 96%, 97%, 98%, 99% or 100% identity with all or a portion of SEQ ID NO. 2. Peptides that have less than 100% identity with all or a portion of SEQ ID NO. 2 will be referred to as "variants." Thus variant peptides include peptides where one or more of the amino acids in the reference sequence is deleted or substituted, or one or more amino acids are inserted into the sequence of the reference amino acid sequence. The amino acid substitutions may be conservative or non-conservative. For example, a tyrosine amino acid substituted with a phenylalanine would be an example of a conservative amino acid substitution, whereas an arginine replaced with an alanine would represent a non-conservative amino acid substitution. The substituted amino acids can be contiguous or non-contiguous substitutions. Percent identity is determined by comparing the amino acid sequence of the variant with the reference sequence using known sequence alignment programs, such as the MEGA-LIGN project in the DNA STAR program.

In one example, the isolated peptide has a sequence that is 98% identical to all or a portion of SEQ ID No. 2.

In another example, the peptide is 100 amino acids in length and has the sequence HLSLTRGLSRTSMKPRSSRG-SIFTFRRRDLGSEADFADDENSTAGESESHRTSLLVP-WPLR RTSAQGQPSPGTSAPGHALHGKKNSTVD-CNGVVSLLGAG, SEQ ID NO: 2.

In another example, the peptide is 40 amino acids in length and has the sequence GSEADFADDENSTAGESESH RTSLLVPWPLRRTSAQGQPS, SEQ ID NO: 4.

In yet another example, the peptide is 20 amino acids in length and has the sequence NSTAGESESHRTSLLVPWPL, SEQ ID NO: 3.

In yet another example, the peptide is 10 amino acids in length and has the sequence set forth in SEQ ID NO: 1.

The peptides are derived from the intracellular domain 1 to 2 linker in the sodium channel protein hNav1.5 having the H558R-SCN5A polymorphism.

Provided herein are isolated polynucleotides encoding the peptides described above.

Accordingly, the one or more isolated polynucleotides encoding a peptides having a sequence that is from 10 to 100 amino acids in length, where the peptide includes the sequence SESHRTSLLV, SEQ ID NO: 1. and is at least 90% identical to all or a portion of SEQ ID NO. 2. Such a peptide can have sequence identity of 90%, 91%, 92%, 93%, 94%, 95%, 96%, 97%, 98%, 99% or 100% identity with all or a portion of SEQ ID NO. 2.

In one example, the isolated polynucleotide encodes a peptide that has a sequence that is 98% identical to all or a portion of SEQ ID No. 2.

In another example, the isolated polynucleotide encodes a peptide that is 100 amino acids in length and has the sequence HLSLTRGLSRTSMKPRSSRGSIFTFRRRDLGS EAD-FADDENSTAGESESHRTSLLVPWPLRRTSAQGQPSP-GTSAPGHALHGKKNSTVDCN GVVSLLGAG, SEQ ID NO: 2. One example of such a polynucleotide has the sequence:

(SEQ ID NO: 5)
catctcagcctcacccgtggcctcagcaggacttctatgaagccacgttc cagccgcgggagcattttcacctttcgcaggcgagacctgggttctgaag cagattttgcagatgatgaaaacagcacagcgggggagagcgagagccac cGcacatcactgctggtgccctggccctgcgccggaccagtgcccaggg acagcccagtcccggaacctcggctcctggccacgccctccatggcaaaa agaacagcactgtggactgcaatggggtggtctcattactgggggcagg c.

In another example, the isolated polynucleotide encodes a peptide that is 40 amino acids in length and has the sequence GSEADFADDENSTAGESESHRTSLLVPWPLR RTSAQ-GQPS, SEQ ID NO: 4. One example of such a polynucleotide has the sequence:

(SEQ ID NO 6)
ggttctgaagcagattttgcagatgatgaaaacagcacagcggggagag cgagagccaccGcacatcactgctggtgccctggccctgcgccggacca gtgcccagggacagcccagt.

In yet another example, the isolated polynucleotide encodes a peptide that is 20 amino acids in length and has the sequence NSTAGESESHRTSLLVPWPL, SEQ ID NO: 3. One example of such a polynucleotide has the sequence:

(SEQ ID NO: 7)
aacagcacagcggggagagcgagagccaccGcacatcactgctggtgcc ctggcccctg.

In yet another example, the isolated polynucleotide encodes a peptide that is 10 amino acids in length and has the sequence set forth in SEQ ID NO: 1. One example of such a polynucleotide has the sequence: gagagccaccGcacatcact-gctggtgccc, (SEQ ID NO: 8).

Also provide are methods of treating a subject that has a genetic predisposition to, or has been diagnosed as having, a cardiac disorder related to dysfunctional sodium channels. The method includes administering to the subject a therapeutically effective amount of one or more of the peptides described above. In another embodiment, the method includes administering to the subject a therapeutically effective amount of one or more polynucleotides encoding one or more of the peptides described above.

In one embodiment, such a subject is a human subject.

Examples of cardiac disorders related to dysfunctional sodium channels include Brugada syndrome, Long QT syndromes, conduction disease, atrial standstill, and sinus node disease. In another example, the subject is a human subject that has been diagnosed as having or has symptoms or characteristics of a patient with heart failure. In some examples, the subject has been diagnosed as having or has symptoms or characteristics of a patient with congestive heart failure Subjects The methods described herein are useful for subjects who are at risk of developing or have been diagnosed as having a cardiac disorder due to dysfunctional protein channels. Such subjects may have a family history of a genetic arrhythmia syndrome. Alternatively, the subjects may have been genotypes and shown to have a mutation on their SCN5A gene. Alternatively, the subjects may present with the typical signs and/or symptoms of a genetic or acquired arrhythmia syndrome. Examples of such cardiac arrhythmias include, but are not limited to: Brugada syndrome, Long QT3 syndrome, conduction disease, atrial standstill, sinus node disease, heart failure, cardiac fibrosis, dilated cardiomyopathy, and arrhythmogenic right ventricular cardiomyopathy.

In one embodiment, the genetic arrhythmia syndrome is Brugada syndrome. "Brugada Syndrome" is well known in the art and can be characterized according to the following: in some cases, the disease can be detected by observing characteristic patterns on an electrocardiogram (ECG or EKG), which may be present all the time, or might be elicited by the administration of particular drugs (e.g., Class IC antiarrythmic drugs that blocks sodium channels and causing appearance of ECG abnormalities—e.g. ajmaline, flecainide) or resurface spontaneously due to as yet unclarified triggers. The pattern seen on the ECG is persistent ST elevations in the electrocardiographic leads V1-V3 with a right bundle branch block (RBBB) appearance with or without the terminal S waves in the lateral leads that are associated with a typical RBBB. A prolongation of the PR interval (a conduction disturbance in the heart) is also frequently seen. The electrocardiogram can fluctuate over time, depending on the autonomic balance and the administration of antiarrhythmic drugs. Adrenergic stimulation decreases the ST segment elevation, while vagal stimulation worsens it. The administration of class Ia, Ic and III drugs increases the ST segment elevation. Exercise decreases ST segment elevation in some patients but increases it in others (after exercise when the body temperature has risen). The changes in heart rate induced by atrial pacing are accompanied by changes in the degree of ST segment elevation. When the heart rate decreases, the ST segment elevation increases and when the heart rate increases the ST segment elevation decreases. However, the contrary can also be observed.

The disease has been linked to the presence of mutations in the α-subunit of the human cardiac sodium channel (hNav1.5). Many previously identified mutations result in a loss of whole cell sodium current. A single mutation in SCN5A, the gene encoding hNav1.5, is sufficient to cause the disease. In some cases though, multiple mutations on SCN5A, which are by themselves benign, can cause the disease.

The mutation R282H-SCN5A, resulting in histidine replacing arginine at amino acid 282 of hNav1.5, is associated with Brugada syndrome. This mutation was found on one allele of a 37-year-old patient (II-2) with a positive BrS flecainide-induced ECG pattern (Pitzalis et al., *J. Am Coll Cardiol.* 2003, 42:1632-7). This individual became the proband for a subsequently tested and genotyped family. The R282H-SCN5A mutation occurs in domain 1 of hNav1.5 in the beginning of the pore forming loop (SS1) (FIG. 1).

Since Brugada syndrome (BrS) is an inherited disorder characterized by ST-segment elevation in right precordial leads, an EKG can be used to determine if the subject has characteristics of a person with BrS. Typically the EKG is done while giving the patient a sodium channel blocker such as flecanide to unmask the disease because the phenotype does not always appear on the EKG under normal condition. Another method for determining if the subject has characteristics of a person with BrS involves genetic testing for the presence of mutations in SCN5A that cause BrS. Accordingly, patients can be genotyped to assess if they carry the H558R polymorphism as well as the mutation.

In another embodiment, the genetic arrhythmia syndrome is long QT syndrome. In congenital long QT syndrome, the electrocardiogram QT interval is prolonged due to dysfunctional ventricular repolarization. Symptoms of LQT syndrome include syncope and sudden death. Variant 3 (LQT-3) is associated with mutations in SCN5A. Arrhythmias in LQT-3 mutation carriers are more likely to occur at rest, when heart rate is slow. Congenital long QT syndrome, a rare disease in which the QT interval of the electrocardiogram is prolonged due to dysfunctional ventricular repolarization, Long QT3 syndrome usually manifests in teenage years, although it can also manifest in adulthood.

In another embodiment, the subject has symptoms or characteristics suggesting or indicating that the subject is at risk of developing, or have been diagnosed as having, heart failure. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rales and the like including laboratory findings associated with heart failure.

The peptides and polynucleotides disclosed herein can be used in methods for treating subjects who have been diagnosed as having, or are at risk of developing, a cardiac disorder. Such methods of treatment include administering to the subject a therapeutically effective amount of one or more peptides or polynucleotides as disclosed herein.

The term "treatment" or grammatical equivalents encompasses the improvement and/or reversal of the symptoms of a cardiac disorder, or the prevention or reduction in the severity of symptoms by reducing or eliminating the likelihood of symptoms occurring in a patient who is at risk for developing the cardiac disorder.

By the phrase "therapeutically effective" amount or related phrase is an amount of administered peptide or polynucleotide needed to achieve a beneficial clinical outcome.

Peptide Therapy

The peptides disclosed herein can be used as a therapeutic composition and delivered to the subject to treat, alleviate or prevent the development, or the severity, of symptoms in the subject. In one embodiment, a peptide is from 10 to 100 amino acids in length and includes the H558R-polymorphism in the SCN5A gene. In certain embodiments, the peptide comprises the sequence of SEQ ID NO: 1 and all or a portion (i.e., from 10 to 99 amino acids) of the sequence of SEQ ID NO: 2.

Also contemplated are methods that employ modified peptides in which one or more amino acids of the present peptides are altered by post-translation processes or synthetic methods. Examples of such modifications include, but are not limited to, glycosylation, iodination, myristoylation, and pegylation. Also contemplated are methods in which the therapeutic composition comprises a fusion protein, e.g., a protein that comprises at least one of the instant peptides and a targeting moiety that targets the therapeutic agent to myocytes. In some instances the targeting moiety is another peptide or protein.

Also contemplated are methods in which the therapeutic composition comprises one of the instant peptides and a moiety that allows uptake of the peptide by a cell, particularly a myocyte.

A variety of methods exist for introducing proteins and polypeptides into cells. Such methods include, but are not limited to, "protein transduction" or "protein therapy" as described in publications by Nagahara et al. (Nagahara, et al., 1998, Nat Med, 4:1449-52.) and in publications from the laboratory of Dowdy (Nagahara, et al., 1998, Nat Med, 4:1449-52.; Schwarze, et al., 1999, Science, 285:1569-72.; Vocero-Akbani, et al., 2000, Methods Enzymol, 322:508-21; Ho, et al., 2001, Cancer Res, 61:474-7.; Vocero-Akbani, et al., 2001, Methods Enzymol, 332:36-49; Snyder and Dowdy, 2001, Curr Opin Mol Ther, 3:147-52.; Becker-Hapak, et al., 2001, Methods, 24:247-56.), publications which are incorporated herein by reference.

Delivery Vehicles for Peptides

Various delivery systems are known and can be used to deliver the present peptides to myocytes, such as encapsulation in liposomes, or controlled release devices. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat (1991). Targeting of liposomes to hepatocytes. *Targeted Diagn. Ther* 4: 87-103). In some embodiments, the liposome comprises a targeting moiety that permits preferential delivery of the peptides to myocytes and/or subsequent internalization of the peptide.

Polynucleotide Therapy

Also provided are methods of treating a subject that has a genetic predisposition to, or has been diagnosed as having, a cardiac disorder related to dysfunctional sodium channels. Such a method includes administering to the subject a therapeutically effective amount of a polynucleotide that encodes one or more of the above-mentioned peptides. Also contemplated are expression vectors that contain the polynucleotides described above.

Polynucleotides encoding and expressing one or more of the present peptides can be introduced into myocardium cells of the subject using a suitable myocardium nucleic acid delivery system. Such a delivery system can use vectors, which are nucleic acid molecules capable of mediating introduction of another nucleic acid or polynucleotide sequence to which it has been linked into a cell. One type of vector is an episome, i.e., a nucleic acid capable of extrachromosomal replication. Other types of vectors become part of the genome of the cell into which they are introduced. Vectors capable of directing the expression of inserted DNA sequences are referred to as "expression vectors" and may include plasmids, viruses, or other types of molecules known in the art.

In one embodiment, the delivery system includes a non-viral vector operably linked to the polynucleotide. Examples of such non-viral vectors include the polynucleoside alone or in combination with a suitable protein, polysaccharide or lipid formulation. For example, DNA encoding and expressing the peptide can be incorporated into liposomes are targeted to and internalized by the cells of the subject.

Polynucleotides encoding the peptides disclosed herein can also be incorporated into plasmids that are introduced into cells of the subject by transfection. The polynucleotides can also be introduced into myocardial cells using viruses. Such viral "vectors" can have DNA or RNA genomes.

Numerous viral vectors are well known to those skilled in the art. Viral vectors that have polynucleotide sequences encoding a polypeptide, for example cloned, into their genomes are referred to as "recombinant" viruses. Transfer of DNA molecules using viruses is particularly useful for transferring polynucleotide sequences into particular cells or tissues of an animal. Such techniques are commonly known in the art as gene therapy.

Examples of a suitable vector for gene therapy include an adenovirus, adenovirus-associated virus (AAV), helper-dependent adenovirus, retrovirus, or hemagglutinating virus of Japan-liposome (HVJ) complex.

Other suitable vectors include viral vectors, fusion proteins and chemical conjugates. Retroviral vectors include moloney murine leukemia viruses and HIV-based viruses. One type of HIV-based viral vector comprises at least two vectors wherein the gag and pol genes are from an HIV genome and the env gene is from another virus. DNA viral vectors can also be used. These vectors include pox vectors such as orthopox or avipox vectors, herpesvirus vectors such as a herpes simplex I virus (HSV) vector [Geller, A. I. et al., *J. Neurochem,* 64: 487 (1995); Lim, F., et al., in DNA Cloning: Mammalian Systems, D. Glover, Ed. (Oxford Univ. Press, Oxford England) (1995); Geller, A. I. et al., *Proc Natl. Acad. Sci.: U.S.A.:* 90 7603 (1993); Geller, A. I., et al., *Proc Natl. Acad. Sci USA:* 87:1149 (1990)], Adenovirus Vectors [LeGal LaSalle et al., *Science,* 259:988 (1993); Davidson, et al., *Nat. Genet* 3:219 (1993); Yang, et al., *J. Virol.* 69:2004 (1995)] and Adeno-associated Virus Vectors [Kaplitt, M. G., et al., *Nat. Genet.* 8:148 (1994)].

In some examples, the adenovirus is of a serotype which is not pathogenic for man. Such serotypes include type 2 and 5 adenoviruses (Ad 2 or Ad 5). In the case of the Ad 5 adenoviruses, the sequences necessary for the replication are the E1A and E1B regions. Methods for preparing adenovirus vectors are described in U.S. Pat. No. 5,932,210, which issued in August, 1999 to Gregory et al., U.S. Pat. No. 5,985,846 which issued in November, 1999 to Kochanek et al, and U.S. Pat. No. 6,033,908 which issued in March, 2000, to Bout et al.

In some examples, the virus vector is an immunologically inert adenovirus. As used herein the term "immunologically inert" means the viral vector does not encode viral proteins that activate cellular and humoral host immune responses. Methods for preparing immunologically inert adenoviruses are described in Parks et al., *Proc Natl Acad Sci USA* 1996; 93(24) 13565-70; Leiber, A. et al., *J. Virol.* 1996; 70(12) 8944-60; Hardy s., et al, *J. Virol.* 1997, 71(3): 1842-9; and Morsy et al, *Proc. Natl. Acad. Sci. USA* 1998. 95: 7866-71, all of which are specifically incorporated herein by reference. Such methods involve Cre-loxP recombination. In vitro, Cre-loxP recombination is particularly adaptable to preparation of recombinant adenovirus and offers a method for removing unwanted viral nucleotide sequences. Replication deficient recombinant adenovirus lacks the E1 coding sequences necessary for viral replication. This function is provided by 293 cells, a human embryonic kidney cell line transformed by adenovirus type. First generation adenoviruses are generated by co-transfecting 293 cells with a helper virus and a shuttle plasmid containing the foreign gene of interest. This results in the packaging of virus that replicates both the foreign gene and numerous viral proteins. More recently, 293 cells expressing Cre recombinase, and helper virus containing essential viral sequences and with a packaging signal flanked by loxP sites, have been developed (See Parks et al.) In this system, the helper virus supplies all of the necessary signals for replication and packaging in trans, but is not packaged due to excision of essential sequences flanked by loxP. When 293-Cre cells are co-transfected with this helper virus, and a shuttle plasmid (pRP1001) containing the packaging signal, nonsense "filler DNA", and the foreign gene, only an adenovirus containing filler DNA and the foreign gene is packaged (LoxAv). This results in a viral recombinant that retains the ability to infect target cells and synthesize the foreign gene, but does not produce viral proteins.

One type of viral vector is a defective adenovirus which has the exogenous polynucleotide sequence inserted into its genome. The term "defective adenovirus" refers to an adenovirus incapable of autonomously replicating in the target cell. Generally, the genome of the defective adenovirus lacks the sequences necessary for the replication of the virus in the infected cell. Such sequences are partially or completely removed from the genome. To be able to infect target cells, the defective virus contains sufficient sequences from the original genome to permit encapsulation of the viral particles during in vitro preparation of the construct. Other sequences that the virus contains are any such sequences that are said to be genetically required "in cis."

Non-defective or replication competent viral vectors can also be used. Such vectors retain sequences necessary for replication of the virus. Other types of vectors are plasmid vectors.

Pox viral vectors introduce the gene into the cell's cytoplasm. Avipox virus vectors result in only a short term expression of the nucleic acid. Adenovirus vectors, adeno-associated virus vectors and herpes simplex virus (HSV) vectors may be indication for some embodiments. The adenovirus vector results in a shorter term expression (eg., less than about a month) than adeno-associated virus, which, in some embodiments, may exhibit much longer expression. The particular vector chosen will depend upon the condition being treated. Various in vivo or ex vivo cardiac administration techniques can be used.

Expression vectors normally contain sequences that facilitate gene expression. An expression vehicle can comprise a transcriptional unit comprising an assembly of a protein encoding sequence and elements that regulate transcription and translation. Transcriptional regulatory elements generally include those elements that initiate transcription. Types of such elements include promoters and enhancers. Promoters may be constitutive, inducible or tissue specific. Transcriptional regulatory elements also include those that terminate transcription or provide the signal for processing of the 3' end of an RNA (signals for polyadenylation). Translational regulatory sequences are normally part of the protein encoding sequences and include translational start codons and translational termination codons. There may be additional sequences that are part of the protein encoding region, such as those sequences that direct a protein to the cellular membrane, a signal sequence for example.

The polynucleotides that are introduced into cells can be expressed at a high level (i.e., the introduced polynucleotide sequence produces a high quantity of the peptide within the cells) after introduction into the cells. Techniques for causing a high-level of expression of polynucleotide sequences introduced into cells are well known in the art. Such techniques frequently involve, but are not limited to, increasing the transcription of the polynucleotide sequence, once it has been introduced into cells. Such techniques frequently involve the use of transcriptional promoters that cause transcription of the introduced polynucleotide sequences to be initiated at a high rate. A variety of such promoters exist and are well known in the art. Frequently, such promoters are derived from viruses. Such promoters can result in efficient transcription of polynucleotide sequences in a variety of cell types. Such promoters can be constitutive (e.g., CMV enhancer/promoter from human cytomegalovirus) or inducible (e.g., MMTV enhancer/promoter from mouse mammary tumor virus). A variety of constitutive and inducible promoters and enhancers are known in the art, such as Rous sarcoma virus (RSV) (Davis, et al., 1993, *Hum Gene Ther* 4:151). Other promoters that result in transcription of polynucleotide sequences in specific cell types, so-called "tissue-specific promoters," can also be used. A variety of promoters that are expressed in specific tissues exist and are known in the art. For example, promoters whose expression is specific to neural, liver, epithelial and other cells exist and are well known in the art and include promoters used to direct gene transfer to cardiac myocytes and are currently being tested in human clinical trials (see below).

Other elements that can enhance expression can also be included such as an enhancer or a system that results in high levels of expression such as a tat gene and tar element. This cassette can then be inserted into a vector, e.g., a plasmid vector such as pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). The vector can also be bound to a nucleic acid binding moiety in a synthetic delivery system, such as the system disclosed in WO 95/22618.

Typically, vectors contain one or more restriction endonuclease recognition sites which permit insertion of the peptide encoding sequence. The vector may further comprise a marker gene, such as for example, a dominant antibiotic resistance gene, which encode compounds that serve to identify and separate transformed cells from non-transformed cells. An example includes the β-lactamase gene for ampicillin resistance.

If desired, the polynucleotides disclosed herein may also be used with a microdelivery vehicle such as cationic liposomes and adenoviral vectors. For a review of the procedures for liposome preparation, targeting and delivery of contents, see Mannino and Gould-Fogerite, BioTechniques, 6:682 (1988). See also, Felgner and Holm, Bethesda Res. Lab. Focus, 11(2):21 (1989) and Maurer, R. A., Bethesda Res. Lab. Focus, 11(2):25 (1989).

Several approaches have been taken to develop specific targeting to the heart. It is generally known in the field that cardiac tissue is especially amenable to gene transfer techniques. (See e.g, Donahue, J. et al. (1998) *Gene Therapy* 5: 630; Donahue, J. et al. *PNAS* (USA) 94: 4664 (disclosing rapid and efficient gene transfer to the heart); Akhter, S. et al. (1997) *PNAS* (USA) 94: 12100 (showing successful gene transfer to cardiac ventricular myocytes); and references cited therein, the entire contents of which are incorporated herein by reference.

One approach is described by Muller et al. (*Cardiovascular Research* 70 (2006) 70-78) where combining transcriptional targeting by the CMVenh/MLC1.5 promoter and Adeno-Associated Virus (AAV) vectors devoid of binding the AAV-2 primary receptor results in an efficient cardiac gene transfer with a significantly reduced hepatic transduction.

Other Adenoviral vectors suitable for use by the methods disclosed herein include (Ad.RSV.lacZ), which includes the Rous sarcoma virus promoter and the lacZ reporter gene as well as (Ad.CMV.lacZ), which includes the cytomegalovirus promoter and the lacZ reporter gene. Methods for the preparation and use of viral vectors are described in U.S. patent application of Rosenzweig, Ser. No. 09/789,894, filed Feb.

21, 2001; WO 96/13597; WO 96/33281; WO 97/15679; and Trapnell et al., *Curr. Opin. Biotechnol.* 5(6):617-625, 1994, the contents of which are incorporated herein by reference.

One example of a myocardium delivery system is a recombinant viral vector that incorporates one or more of the polynucleotides therein, can have a pfu (plague forming units) of from about $10^8$ to about $5 \times 10^{10}$ pfu. In embodiments in which the polynucleotide is to be administered with a non-viral vector, use of between from about 0.1 nanograms to about 4000 micrograms, or from about 1 nanogram to about 100 micrograms, will often be useful.

Choice of a particular myocardium delivery system will be guided by recognized parameters including the cardiac arrhythmia of interest and the amount and length of expression desired. Suitable virus vectors approved for human applications include adenovirus or vectors that are undergoing human clinical trials of cardiac gene therapy.

For example, gene therapy clinical trials are currently under way to determine the feasibility of giving a recombinant adeno-associated viral vector (AAV), which consists of an AAV serotype 1 capsid and contains the human SERCA2a cDNA flanked by Inverted Terminal Repeats (ITR) derived from AAV serotype 2 (AAV1/SERCA2a). The vector expresses the sarcoplasmic reticulum calcium ATPase (SERCA2a), driven by the CMV promoter (AAV6-CMV-SERCA2a), and subjects include heart failure patients that have received a left ventricular assist device (LVAD). The purpose of gene transfer of SERCA2a is to improve systolic and diastolic function of the failing ventricle. Studies show that reduction of SERCA2a in failing ventricle is a key factor in depression of contraction, and that restoration of SERCA2a levels can improve function to near normal levels. The vector will be delivered during a cardiac catheterisation procedure by a 10-minute infusion into the coronary arteries. Two companion studies, one using SERCA2a gene transfer with the same vector, but delivered by direct injection into the myocardium during LVAD insertion, and another using AAV1-CMV-SERCA2a delivered percutaneously in heart failure patients, are also under way.

In certain embodiments, the therapeutic agent is incorporated into a pharmaceutical composition that can be in the form of a pyrogen-free, parenterally-acceptable, aqueous solution. The preparation of such parenterally-acceptable solutions, having due regard to pH, isotonicity, stability, and the like, is within the level of ordinary skill in the art of pharmacology. In one example, the pharmaceutical composition for injection should contain, in addition to the vector, an isotonic vehicle such as Sodium Chloride Injection, Ringer's Injection, Dextrose Injection, Dextrose and Sodium Chloride Injection, Lactated Ringer's Injection, phosphate buffered saline (PBS), or other vehicle as known in the art. The pharmaceutical composition used in the method disclosed herein also contain stabilizers, preservatives, buffers, antioxidants, or other additives known to those of skill in the art.

Methods employing herpesvirus, catheter systems, and adenovirus to deliver polynucleotides to cardiac cells are also described in U.S. Pat. No. 6,846,670, U.S. Pat. No. 6,717,196, and U.S. Pat. No. 6,436,907. Each of these methods is incorporated herein in its entirety.

Administration

Methods disclosed herein are broadly compatible with one or a combination of different administration (delivery) systems. Generally, the peptides or polynucleotides disclosed herein can be included in a therapeutic composition for administration to the myocardium of the subject. The therapeutic compositions provided herein contain one or more peptides or polynucleotides of the present provided herein together with a therapeutically acceptable carrier.

In certain embodiments, the therapeutic composition is administered by injection. Other modes of administering the therapeutic composition to the subject include, but are not limited to, implantation of controlled release delivery devices, application of patches containing the peptide or polynucleotide, etc.

For example, one suitable administration route includes perfusing the therapeutic composition containing the peptide or polynucleotide into cardiac vasculature. If desired, the administration step can further include increasing microvascular permeability using routine procedures, typically administering at least one vascular permeability agent prior to or during administration of the gene transfer vector. Examples of particular vascular permeability agents include administration of one or more of the following agents, which may be in combination with a solution having less than about 500 micromolar calcium: substance P, histamine, acetylcholine, an adenosine nucleotide, arachidonic acid, bradykinin, endothelin, endotoxin, interleukin-2, nitroglycerin, nitric oxide, nitroprusside, a leukotriene, an oxygen radical, phospholipase, platelet activating factor, protamine, serotonin, tumor necrosis factor, vascular endothelial growth factor, a venom, a vasoactive amine, or a nitric oxide synthase inhibitor. Particular compositions for this use include serotonin, vascular endothelial growth factor (VEGF), or a functional VEGF fragment to increase the permeability.

Typical perfusion protocols in accord with the methods provided herein are generally sufficient to transfer the peptide or polynucleotide to at least about 10% of cardiac myocytes in the subject. Infusion volumes of between from about 0.5 to about 500 ml are useful in some embodiments. Also suitable are coronary flow rates of between from about 0.5 to about 500 ml/min. Other perfusion protocols involve the AV nodal artery. Transformed heart cells, typically cardiac myocytes that include the polynucleotide may be suitably positioned at or near the AV node. Various methods of administration to cardiac myocytes are described in U.S. patent to Donahue, et al., U.S. Pat. No. 7,034,008, Apr. 25, 2006, the entire contents of which are incorporated herein by reference.

Dosage

Initially, the correct dosage is determined using in vitro studies and in animal studies. For example the correct dosage can be estimated using HEK 293 cells expressing the peptide and the mutant sodium channel that causes BrS. Correct dosage can also be estimated using a dog model of heart failure.

The amount of peptide or nucleic acid used in the methods provided herein will depend upon the nature and severity of the condition being treated, on the nature of prior treatments which the patient has undergone, the patient and his or her clinical condition, weight, age, sex, etc. In some embodiments, the amount of nucleic acid encoding the peptide is from about 0.001 ng to about 1 mg per kg body weight. Initially, the attending physician will administer low doses of the composition and observe the patient's response. Larger doses of composition may be administered until the optimal therapeutic effect is obtained for the patient, and at that point the dosage is not increased further. It may be desirable to administer simultaneously or sequentially a therapeutically effective amount of one or more of the therapeutic compositions disclosed herein to one individual as a single treatment episode. Ultimately, the attending physician will decide the amount of therapeutic composition with which to treat each individual patient.

Illustrative strategies for detecting modulation of treated or transformed heart include performing a conventional electrocardiogram (ECG). Modulation of cardiac electrical properties by use disclosed herein is readily observed by inspection of the ECG. The therapeutic composition, i.e., the peptide or the polynucleotide is administered to the subject in an amount sufficient to show a meaningful subject or patient benefit. For example, if the patient has BrS, one may do an EKG to determine if a change in the ST-segment elevation in right precordial leads has occurred. Other methods of evaluating treated heart cells are described in U.S. patent application of Rosenzweig, Ser. No. 09/789,894, filed Feb. 21, 2006.

If the patient has heart failure, the effective amount may be determined by monitoring for an improvement in heart function (mainly pump caused by an improvement in the conduction system). In the case of heart failure, "improvement in heart function" may be assessed using any of the measurements described herein (e.g., measurement of ejection fraction, fractional shortening, left ventricular internal dimension, heart rate, etc.), as well as any effect upon the subject's survival. A compound which causes an improvement in any parameter associated with heart failure used in the screening methods provided herein may thereby be identified as a therapeutic compound.

The duration of therapy with the therapeutic compositions used in the methods provided herein will vary, depending on the unique characteristics of the pharmaceutical composition and the particular therapeutic effect to be achieved, the severity of the disease being treated and the condition and potential idiosyncratic response of each individual patient. Ultimately the attending physician will decide on the appropriate duration of therapy with the pharmaceutical composition used in the methods provided herein.

Methods of Predicting Prognosis

Also provided are methods of predicting the occurrence of a cardiac event in a subject, by testing the subject for the presence of H558R-polymorphism on the subject's SCN5A gene. Accordingly, detecting the presence of the H558R-polymorphism in the subject is predictive that the cardiac event is less likely to occur.

Also provided are methods of predicting the severity or prognosis of cardiac symptoms in a subject, wherein the subject has either (a) been diagnosed as having a cardiac disorder, (b) is suspected of developing a cardiac disorder. The method includes testing the subject for the presence of H558R-polymorphism on the subject's SCN5A gene, wherein the presence of the H558R-polymorphism is predictive of less severe cardiac symptoms or better prognosis in the subject. In one example of this method, the prediction of better prognosis in the subject includes prediction of response to therapy.

The methods described herein are useful for subjects who have either (a) been diagnosed as having a cardiac disorder, or (b) are suspected of developing a cardiac disorder. Such subjects may have a family history of a genetic arrhythmia syndrome. Alternatively, the subjects may have been genotypes and shown to have a mutation on their SCN5A gene. Alternatively, the subjects may present with the typical signs and/or symptoms of a genetic or acquired arrhythmia syndrome. In one embodiment of the predictive methods described above, the cardiac disorder is due to dysfunctional sodium channels in the heart. Such dysfunctional sodium channels can give rise to cardiac arrhythmias. Examples of such cardiac arrhythmias include, but are not limited to: Brugada syndrome, Long QT3 syndrome, conduction disease, atrial standstill, sinus node disease, heart failure, cardiac fibrosis, dilated cardiomyopathy, and arrhythmogenic right ventricular cardiomyopathy.

A "cardiac event" can be any sign or symptom associated with a cardiac disorder as described. Examples of such cardiac events include, but are not limited to, an episode of cardiac arrhythmia, syncope, atrial fibrillation, ventricular fibrillation or cardiac arrest.

In one example, the subjects at risk have one or more disease-causing mutations on one allele of the SCN5A gene. Examples of such mutation include the mutations causing inherited arrhythmia such as Brugada's and LQT3 syndromes. Examples of such mutations include, but are not limited to, R282H-SCN5A mutation, or SCN5A-P2006A mutation. In such subjects, the presence of the H558R-polymorphism on their SCN5A gene suggests that the subject is less likely to have a cardiac event, or that the subject will have less severe symptoms, a better prognosis, or better response to therapy.

The beneficial H558R-polymorphism may be present in either the same allele that carries the disease-causing mutation, or on another allele. In some subjects, for example some subjects carrying Brugada syndrome mutations, the beneficial effect is seen if the H558R-polymorphism is present on an allele that is not the same as the allele carrying the disease-causing mutation. In other subjects, the beneficial effect of the polymorphism is seen if the polymorphism is present on the same allele that carries the disease-causing mutation.

The present invention will be better understood by reference to the following examples which are offered by way of illustration not limitation.

EXAMPLE 1

SCN5A Polymorphism Restore Trafficking of a Brugada Syndrome Mutation on a Separate Gene Summary: Brugada syndrome (BrS) is associated with a high risk of sudden cardiac death and is caused by mutations in the cardiac voltage-gated sodium channel gene. Priori et al. (*Circulation.* 2002; 105:1342-1347) identified the R282H-SCN5A mutation in the sodium channel gene in patients with Brugada syndrome. In this study, we evaluated a family carrying the R282H-SCN5A mutation. We found that an asymptomatic individual had a common H558R-SCN5A polymorphism and the mutation on separate chromosomes. Therefore, we hypothesized that the polymorphism could rescue the mutation.

In heterologous cells, expression of the mutation alone did not produce sodium current. However, coexpressing the mutation with the polymorphism produced significantly greater current than coexpressing the mutant with the wild-type gene, demonstrating that the polymorphism rescues the mutation. Using immunocytochemistry, we demonstrated that the R282H-SCN5A construct can traffic to the cell membrane only in the presence of the H558R-SCN5A polymorphism. Using fluorescence resonance energy transfer and protein fragments centered on H558R-SCN5A, we demonstrated that cardiac sodium channels preferentially interact when the polymorphism is expressed on one protein but not the other.

This study suggests a mechanism whereby the Brugada syndrome has incomplete penetrance. More importantly, this study suggests that genetic polymorphisms are a potential target for future therapies aimed at rescuing specific dysfunctional protein channels. This example is based on an article by Poelzing et al. (2006) published in *Circulation* 114:368-376.

Introduction: Brugada syndrome (BrS) is an inherited disorder characterized by ST-segment elevation in right precordial leads and increased susceptibility to ventricular arrhythmias and sudden cardiac death. The disease has been linked to the presence of mutations in the α-subunit of the human cardiac sodium channel (hNav1.5). Many previously identified mutations result in a loss of whole-cell sodium current. Earlier studies demonstrated that a single mutation in SCN5A, the gene encoding hNav1.5, is sufficient to cause the disease. In some cases, however, multiple mutations on SCN5A, which are by themselves benign, can cause the disease. Although BrS is an autosomal dominant disease, it is characterized by incomplete penetrance, a phenomenon still incompletely understood. Therefore, although the mutation is phenotypically expressed in most individuals with the mutation, there are individuals in families with BrS who have a mutation but are asymptomatic.

One specific SCN5A missense mutation (R282H-SCN5A) was first identified by Priori et al (*Circulation*. 2002; 105: 1342-1347) in a group of patients with BrS diagnosed by ST-segment elevation in right precordial leads at baseline or during administration of a sodium channel blocker. This mutation, resulting in histidine replacing arginine at amino acid 282 of hNav1.5, was found on 1 allele of a 37-year-old patient (patient II-2) with a positive BrS flecainide-induced ECG pattern. This individual became the proband for a subsequently tested and genotyped family (FIG. 1A). The R282H-SCN5A mutation occurs in domain 1 of hNav1.5 in the beginning of the pore-forming loop (SS1) (FIG. 1B). Importantly, the patient's daughter, who was asymptomatic and did not have a typical BrS ECG pattern either at baseline or after administration of flecainide (patient III-1),[10] was a carrier of the R282H-SCN5A mutation. Further genotyping determined that the subject's second allele had the common H558R-SCN5A polymorphism, which is located in the intracellular domain 1 to 2 linker (FIG. 1B). Therefore, we hypothesized that the H558R-SCN5A polymorphism could suppress or attenuate expression of BrS ECG alterations related to the R282H-SCN5A mutation by rescuing the mutation. The purpose of this report is 3-fold: (1) to demonstrate that coexpressing the R282H-SCN5A mutation and the H558R-SCN5A polymorphism produces fully functional sodium currents similar to control, (2) to assess whether the R282H-SCN5A mutation results in loss of trafficking to the membrane and is restored in the presence of the H558R-SCN5A polymorphism, and (3) to investigate the mechanism by which the H558R-SCN5A polymorphism rescues the R282H-SCN5A mutation.

Methods

Genotyping: Molecular analyses on the SCN5A gene were performed according to our previous article. (Pitzalis M V, et al., *J Am Coll Cardiol.* 2003; 42:1632-1647). Our local Ethics Committee approved the study, and written informed consent was obtained from the participants.

Cloning of SCN5A Mutants and Polymorphisms: The R282H-SCN5A, H558R-SCN5A, and C373Y mutations were created on the hNa$_v$1.5 background (PubMed Accession No. NM 198056) expressed in the GFP-IRES vector (BD Biosciences Clone-tech, San Jose, Calif.) using the Stratagene QuikChange XL Site-Directed Mutagenesis Kit. R282H-SCN5A-FLAG was generated as previously described (Baroudi G, et al., *Circ Res.* 2001; 88:E78-E83). hNav1.5 protein fragments were expressed in the pECFP-N3 or pEYFP-N3 vector (BD Biosciences Clonetech).

Expression of hNav1.5 in HEK293 Cells: Transient transfections of SCN5A expressed in GFP-IRES were performed in human embryonic kidney cells (HEK293) with the Polyfect transfection kit (Qiagen, Valencia, Calif.) according to the manufacturer's protocol for 24 hours.

Electrophysiology: Macroscopic sodium currents from transfected cells were recorded using the whole-cell configuration of the patch-clamp technique as previously described. (Deschenes I, et al., *Cardiovasc Res.* 2000; 46:55-65). Cells that emitted green fluorescence and expressed $I_{Na}$-like currents were considered to express mutants and/or polymorphisms of hNav1.5. Patch electrodes were made from 8161 Corning glass (Dow-Corning, Midland, Mich.). Low-resistance electrodes (<2 MΩ) were used, and a routine-series resistance compensation of an Axopatch 200A was performed to values >80% to minimize the voltage-clamp errors. Voltage-clamp command pulses were generated by a microcomputer using PCLAMP software version 9.02 (Axon Instruments, Foster City, Calif.). To stabilize the current, experiments were performed 10 minutes after entering whole-cell configuration. Membrane currents were filtered at 5 kHz and digitized with 12-bit resolution. The internal solution contained (in mmol/L) NaCl 35, CsF 105, EGTA 10, and Cs-HEPES 10 adjusted to pH 7.4. The bath solution contained (in mmol/L) NaCl 140, KCL 5, MgCl$_2$ 1, CaCl$_2$ 2, HEPES 10, and glucose 10 adjusted to pH 7.4. Experiments were performed at room temperature (22° C. to 23° C.).

Whole-cell sodium current densities were made by holding the resting membrane potential at −120 mV and stepping in 10-mV intervals from −80 to 30 mV. Time course of recovery from inactivation (Tec) was studied using a 2-pulse protocol with a 30-ms prepulse to −30 mV with varying rest intervals at −120 mV, followed by a 30-ms test pulse to −30 mV. Peak current amplitude was fit to the following equation:

$$I_{test}/I_{pre-pulse} = 1-\exp(-t/T_{rec})$$

Voltage dependence of steady-state inactivation was determined by 500-ms prepulses ranging from −140 to −30 mV. Peak current was fit to a Boltzmann distribution:

$$I/I_{max} = (1+\exp[(V-V_{1/2})/kv])^{-1}$$

Image Analysis and Calculation of Fluorescence Resonance Energy Transfer Ratios: Images were acquired with an Olympus IX71 fluorescent microscope that was fitted with a Hamamatsu ORCA-ER charge-coupled device (12 bit) and controlled by the SLIDEBOOK software package from Intelligent Imaging Innovations (Denver, Colo.). Filter-cube specifications for the fluorescent channels were as follows for excitation and emission, respectively: enhanced cyan fluorescent protein (ECFP), 430±25 and 470±30 nm; enhanced yellow fluorescent protein (EYFP), 500±20 and 535±30 nm; and fluorescence resonance energy transfer (FRET), 430±25 and 535±30 nm. The beam splitter was the Chroma 86002v2bs multiband beam splitter for ECFP and EYFP (Rockingham, Vt.).

Image analysis involved 3 basic operations: subtraction of background autofluorescence and blurred light, quantification of fluorescence intensity, and calculation of a corrected FRET (FRETc) calculated by the following equation:

$$FRETc = (I_{DA} - aI_{AA} - dI_{DD})/I_{AA},$$

where $I_{DA}$ is the fluorescence intensity from the FRET filter set and $I_{DD}$ and $I_{AA}$ are the fluorescent intensities from ECFP (the donor) and EYFP (the acceptor), respectively. The crosstalk coefficients a and d are considered constant. The corrected FRET ratio was defined as FRETc/$I_{DD}$.

Immunocytochemistry: Transfected cells were permeabilized with 0.1% Triton into 1 mmol/L PBS/0.5% BSA solution before antibody incubation. Cells were fixed with an acetone/methanol solution (1:3) for 20 minutes. The primary antibody was a mouse anti-FLAG M2 (1:4000) (Stratagene, La Jolla, Calif.). The secondary antibody was a conjugated AffiniPure goat anti-mouse (1:250) (Molecular Probes, Eugene, Ore). Confocal fluorescent images were obtained with a Leica laser scanning confocal microscope (×40 oil immersion lens, airy 1 pinhole).

Statistical Analysis: Statistical analysis of the data were performed with a 2-tailed Student t test for paired and unpaired data or a single-factor ANOVA. A value of P<0.05 was considered statistically significant. All values are reported as mean ±SD unless otherwise noted.

Results

Figure 2:
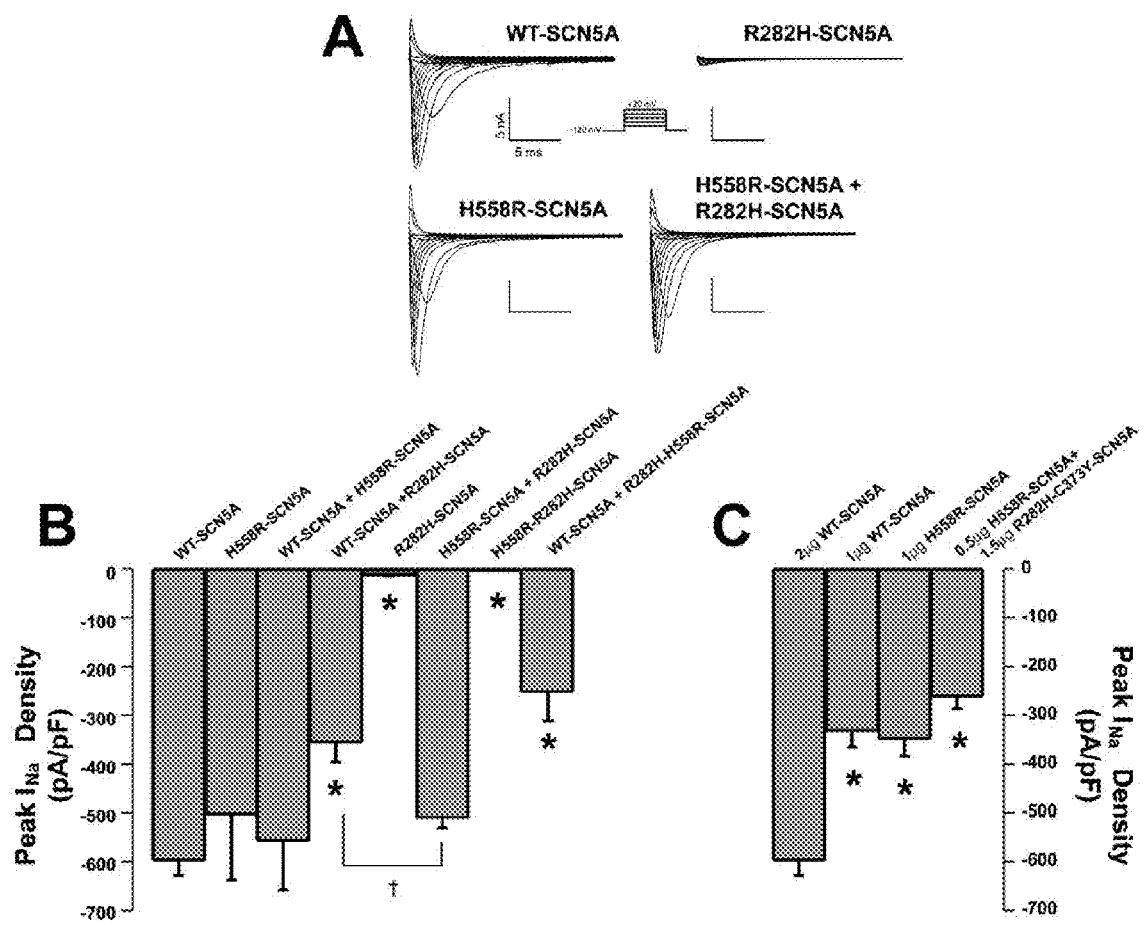
FIG. 2. Whole-cell sodium currents. A, HEK293 cells with WT-SCN5A and H558R-SCN5A have similar whole-cell sodium current amplitudes. The R282H-SCN5A mutation alone does not produce significant whole-cell sodium currents. The H558R-SCN5A polymorphism coexpressed with the R282H-SCN5A mutation (H558R-SCN5A+R282H-SCN5A) produces whole-cell currents of similar amplitude to WT-SCN5A channels alone, suggesting that the H558R-SCN5A polymorphism rescues the R282H-SCN5A mutation. B, Peak sodium current densities. WT-SCN5A (n=9), H558R-SCN5A (n=10), WT-SCN5A+H558R-SCN5A (n=5), and H558R-SCN5A+R282HSCN5A (n=14) whole-cell current densities are similar. WT-SCN5A+R282H-SCN5A (n=8) produced reduced sodium currents compared with WT-SCN5A. R282H-SCN5A (n=12) alone produced no current. Expression of the H558R polymorphism and the R282H mutation on the same construct (n=9) did not produce functional channels (R282H-H558R-SCN5A). WT-SCN5A+R282H-H558RSCN5A (n=9) produced reduced sodium currents compared with WT-SCN5A. C, Varying SCN5A concentration varies whole-cell peak current. WT-SCN5A (1 μg; n=5) and H558R-SCN5A (1 μg; n=6) significantly reduced peak current by ≈45% compared with WT-SCN5A (2 μg). H558R-SCN5A (0.5 μg) and R282H-SCN5A (1.5 μg; n=23) reduced peak current by 54% compared with WT-SCN5A (2 μg; *P<0.05 vs WT-SCN5A; †P<0.05). Error bars expressed as SD.

Effect of Coexpressed H558R-SCN5A and R282H-SCN5A: To determine whether coexpressing the H558R-SCN5A polymorphism with the R282H-SCN5A mutation produces fully functional currents similar to control, sodium currents were recorded from HEK293 cells transfected with wild-type (WT)-SCN5A, H558R-SCN5A, R282H-SCN5A, or a combination of H558R-SCN5A and R282H-SCN5A sodium channels produced on an hNav1.5 background (PubMed Accession No. NM 198056). Cells were transfected and incubated for 24 hours at 37° C. FIG. 2A shows representative current traces from cells transfected with WT-SCN5A (2 μg). When the R282H-SCN5A mutation was expressed alone (2 μg R282H-SCN5A DNA), little to no whole-cell sodium current was recorded (FIG. 2A). The lack of whole-cell currents produced by the R282H-SCN5A mutation is consistent with other BrS mutations. The R282HSCN5A mutation (1 μg) coexpressed with WT-SCN5A channels (1 μg) (WT-SCN5A+R282H-SCN5A) resulted in significantly reduced whole-cell currents corresponding to 58% of WT-SCN5A values (P=0.0009) (FIG. 2B). The H558R-SCN5A polymorphism alone (2 μg) produced fully functional channels with currents and function similar to WT-SCN5A (FIG. 2 and the Table). The H558R-SCN5A polymorphism (1 μg) coexpressed with WT-SCN5A channels (1 μg) (WT-SCN5A+H558R-SCN5A) also produced functional sodium channels with biophysical properties similar to WT-SCN5A channels alone. The total DNA transfected was equal to the 2 μg WT-SCN5A referenced as the control. Importantly, when the H558R-SCN5A polymorphism (1 μg) was coexpressed with the R282H-SCN5A mutation (1 μg) (H558R-SCN5A+R282H-SCN5A), whole-cell sodium currents were similar to WT-SCN5A (2 μg) levels. H558R-SCN5A+R282H-SCN5A current was significantly greater than WT-SCN5A+R282H-SCN5A (P=0.03). Furthermore, the H558R-SCN5A+R282H-SCN5A currents had recovery and steady-state inactivation kinetics similar to WT-SCN5A currents (Table 1). Peak current densities are summarized in FIG. 2B for all combinations of WTSCN5A and mutant channels.

TABLE 1

Peak Current, Recovery From Inactivation, and Steady-State Inactivation Parameters of Whole-Cell Sodium Current

| Na Channels hNav1.5 | Peak Current Density (pA/pF) | Recovery From In-activation ($T_{rec}$), ms | Steady-State Inactivation ($V_{1/2}$), mV |
|---|---|---|---|
| WT-SCN5A | −595 ± 55 | 22.7 ± 2.1 | −93.8 ± 3.4 |
| H558R-SCN5A | −486 ± 61 | 17.6 ± 0.9 | −96.4 ± 3.6 |
| WT-SCN5A+H558R-SCN5A | −568 ± 71 | 17.6 ± 2.0 | −91.9 ± 2.9 |
| WT-SCN5A+R282H-SCN5A | −353 ± 34* | 16.7 ± 2.4 | −96.3 ± 3.5 |
| H558R-SCN5A+R282H-SCN5A | −444 ± 49 | 19.4 ± 1.9 | −96.0 ± 4.7 |
| H558R-SCN5A+R282H-C373Y-SCN5A+ MTSET | −259 ± 65* | 17.5 ± 1.8 | −93.1 ± 3.4 |

Functional indexes of hNav1.5 whole-cell current. The R282H-SCN5A mutation produces a significant decrease only in peak current density. All other biophysical properties are similar between groups.
*P < 0.05.

Previous studies demonstrated that some cases of BrS require 2 mutations on a single gene (cis). (Baroudi G, et all., Circ Res. 2002; 90:E11-E16.) Furthermore, other studies demonstrated that the H558R-SCN5A polymorphism can modulate effects of mutants T5121 and M1766L when expressed on the same construct. (Viswanathan P C, et al., J Clin Invest. 2003; 111:341-346; Ye B, et al., Physiol Genomics. 2003; 12:187-193.) However, in our study, expression of the R282H-SCN5A mutation with the H558R-SCN5A polymorphism on the same hNav1.5 background (R282H-H558R-SCN5A) (2 μg) did not produce functional sodium channels (FIG. 2B). Therefore, it is unlikely that the R282H-SCN5A mutation is somehow integrated into the same protein channel containing the H558R-SCN5A polymorphism when the mutations are present on separate SCN5A sequences. Furthermore, it is important to note that WT-SCN5A+R282H-H558R-SCN5A could not restore whole-cell sodium currents to WT levels alone (FIG. 2B). Specifically, WT-SCN5A could not rescue R282H-H558R-SCN5A.

The $\beta_1$-subunit also may influence protein trafficking as suggested by Biskup et al., Nat Biotechnol. 2004; 22:220-224. However, coexpressing the 131-subunit with WT-SCN5A+R282H-SCN5A or H558RSCN5A+R282H-SCN5A did not significantly alter the principal finding of the study that only H558R-SCN5A was capable of restoring the function of the R282H-SCN5A mutation (data not shown).

The whole-cell peak current density of heterologously expressed proteins often is criticized because it assumes a correlation between the amount of DNA transfected and the amount of current and/or protein produced. Therefore, the apparent restoration of R282H-SCN5A by H558R-SCN5A could be a result of greater transfection efficiency of H558RSCN5A and reduced efficiency of R282H-SCN5A. Transfecting cells with either 1 μg WT-SCN5A or 1 μg H558RSCN5A produced significantly less peak current densities (−322±28 and −332±34 pA/pF, respectively) compared with 2 μg WT-SCN5A (−595±55 pA/pF), which corresponds to a 45% reduction in peak current density (FIG. 2C). These results suggest that whole-cell peak current densities of H558R-SCN5A and WT-SCN5A are related to the amount of DNA transfected.

Concentration of H558R-SCN5A Determines R282H-SCN5A Rescue: To further verify the correlation between the amount of DNA transfected and current density and to determine the relationship of R282H-SCN5A rescue by H558R-SCN5A, 1.5 μg R282H-SCN5A was coexpressed with 0.5 μg H558RSCN5A. Peak current density was reduced by 54.8% to −231±22 pA/pF (P=9×10$^{-5}$) under these conditions (FIG. 2C). These data suggest that there is a 1:1 ratio between the concentration of H558R-SCN5A channels and R282HSCN5A channels because when the amount of H558RSCN5A is reduced by half, the peak current density decreases by 50% regardless of increases in R282H-SCN5A. These data also are consistent with the aforementioned findings in which 1 μg H558R-SCN5A and 1 μg R282H-SCN5A produced peak current densities similar to 2 μg WT-SCN5A. Therefore, these data suggest that the H558R-SCN5A protein interacts with the R282H-SCN5A protein because the concentration of H558R-SCN5A protein is the limiting factor underlying the peak whole-cell current density.

Figure 3:
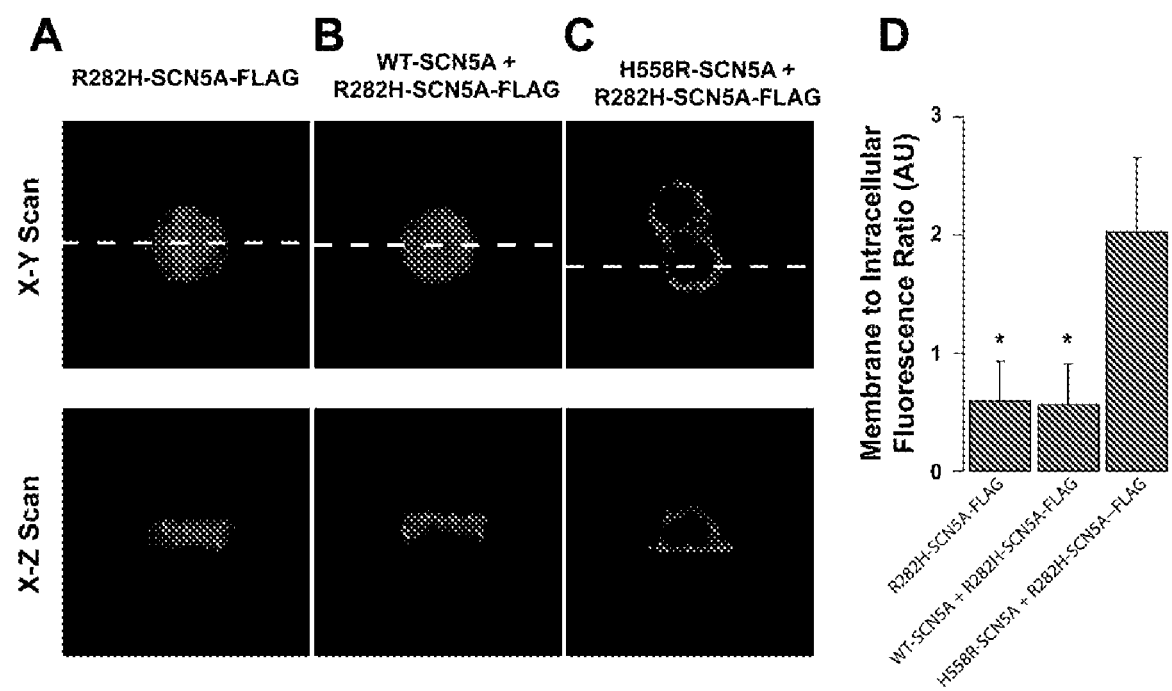
FIG. 3. R282H-SCN5A is a trafficking mutation. A, Top, Confocal immunofluorescence reveals R282H-SCN5A-FLAG staining in internalized compartments of a cell transfected with R282H-SCN5A-FLAG (red signal). Bottom, Z-scan image from the dashed white line in the top panel demonstrates FLAG staining within intracellular compartments. B, Cells transfected with WT-SCN5A+R282H-SCN5A-FLAG reveal FLAG staining also in internalized compartments. C, H558R-SCN5A+R282H-SCN5AFLAG reveals strong FLAG staining in the cell membrane in an X-Y confocal image (top) and Z-scan image (bottom) from the white dashed line in the top panel. D, Summary data demonstrate that R282H-SCN5AFLAG and WT-SCN5A+R282H-SCN5AFLAG membrane staining is significantly reduced compared with H558RSCN5A+R282H-SCN5A-FLAG (n=10 for each group; * P<0.0001).

R282H-SCN5A Protein Trafficking: To determine whether the R282H-SCN5A mutation is a functional or trafficking mutation, the R282H mutation was created on the SCN5A-FLAG construct in which the tag epitope FLAG was inserted in the S5-to-S6 extracellular loop of domain 1. (Baroudi G, et al., Circ Res. 2001; 88:E78-E83.) Confocal immunofluorescence revealed that R282H-SCN5A-FLAG staining produces protein localized in internalized compartments of a representative cell (FIG. 3A). Likewise, coexpressing WT-SCN5A+ R282H-SCN5AFLAG revealed FLAG staining in internalized compartments, consistent with the inability of WT-SCN5A to rescue R282HSCN5A. Importantly, coexpressing H558R-SCN5A+R282H-SCN5A-FLAG resulted in significant FLAG staining in internalized compartments of the cell and around the perimeter of the cell (FIG. 3C). Summary data in FIG. 3D demonstrate that the average fluorescence intensity per unit area in the membrane divided by the average fluorescence intensity per unit area in intracellular compartments (membrane to intracellular fluorescence ratio) is significantly reduced in the R282H-SCN5A and WT-SCN5A+R282HSCN5A-FLAG groups compared with the H558RSCN5A+R282H-SCN5A-FLAG group (n=10 for all groups; $P=6\times10^{-6}$), consistent with R282H-SCN5A rescue by H558R-SCN5A. These data demonstrate that R282HSCN5A-FLAG produces a trafficking-deficient protein that is rescued only when H558R-SCN5A also is present in the cell. However, it was still unclear whether the rescued R282HSCN5A produced functional protein in the membrane.

Figure 4:
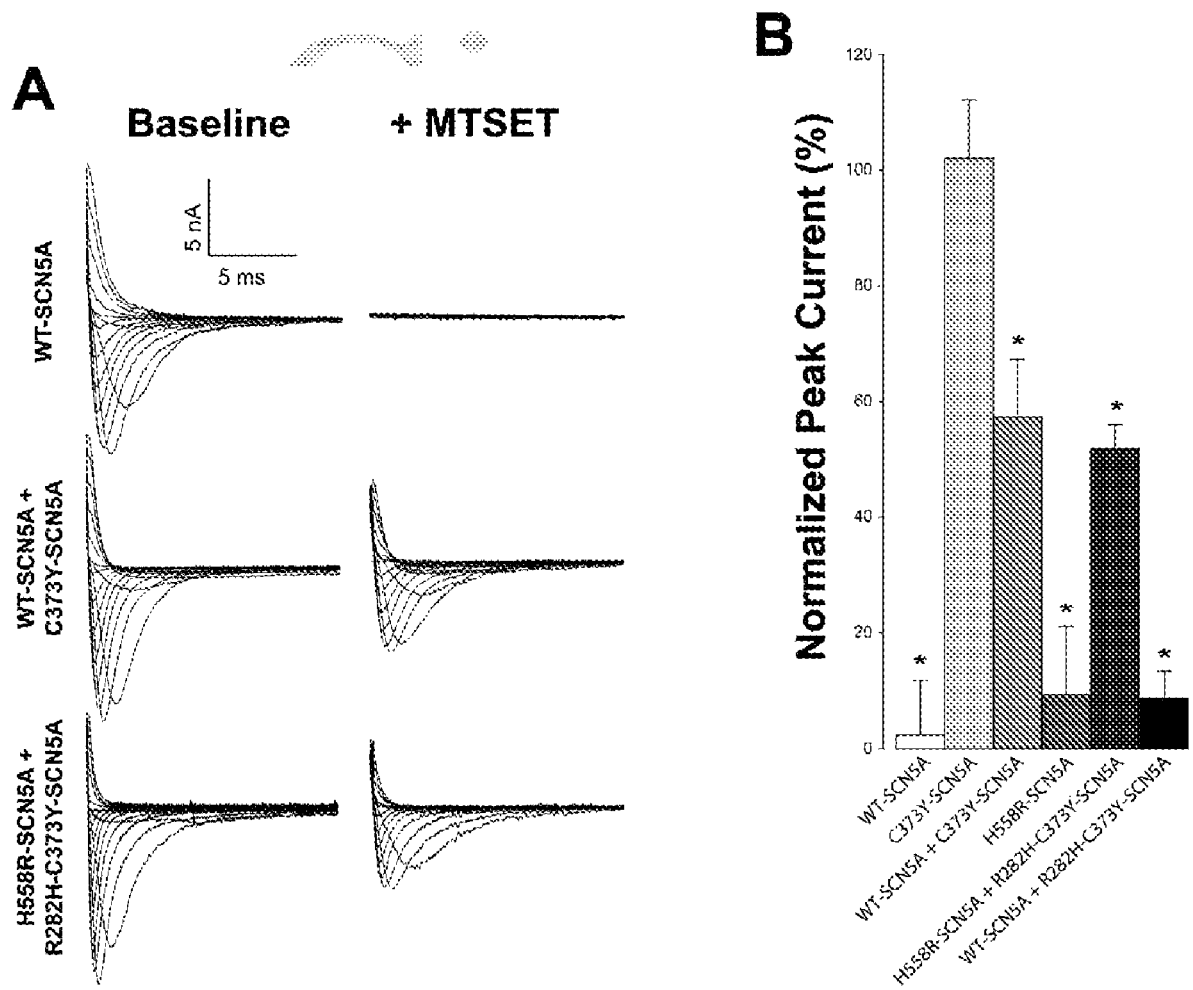
FIG. 4. The H558R-SCN5A polymorphism rescues the R282H-SCN5A mutation by increasing R282H-SCN5A membrane trafficking. A, MTSET application blocks all WT-SCN5A and reduces peak current of WT-SCN5A+C373Y-SCN5A and H558R-SCN5A+R282H-C373YSCN5A channels. B, MTSET blocks almost all WT-SCN5A (n=6), H558RSCN5A (n=5), and WT-SCN5A+R282HC373Y-SCN5A (n=4) channels. MTSET does not block C373Y-SCN5A channels (n=4). Whole-cell current is reduced by 50% during application of MTSET to WT-SCN5A+C373Y-SCN5A (n=5) and H558R-SCN5A+R282H-C373Y-SCN5A (n=12). Error bars expressed as SD.

A complementary approach was developed to determine whether channels with the R282H-SCN5A mutation were trafficking to the membrane and functional in the presence of the H558R-SCN5A polymorphism. A second mutation (C373Y) was added to WT-SCN5A channels. Changing the hNav1.5 amino acid 373 from cysteine to tyrosine is expected to decrease channel sensitivity to extracellular application of [2-(trimethylammonium) ethyl]methanethiosulfonate bromide (MTSET), which blocks channels by binding to cysteine at residue 373. Using MTSET reagents to bind to pore cysteines is an established technique for preferentially blocking sodium channels and other channels such as Kir2.1 potassium channels to assess for their presence and functionality of the channel in the cell membrane. C373 is located in domain 1 of hNav1.5 in the pore-forming loop (SS2) before S6 (FIG. 1B). Representative recordings of whole-cell sodium currents in FIG. 4A demonstrate the effects of 1 μmol/L MTSET on WT-SCN5A, WT-SCN5A+C373YSCN5A, and H558R-SCN5A+R282H-C373Y-SCN5A channels. MTSET blocked all the current in cells expressing WT-SCN5A hNav1.5 protein alone because the MTSET could bind to the cysteine at position 373. This result is summarized in FIG. 4B, which demonstrates that MTSET blocks 98±4% of WT-SCN5A channels (2 μg). These data are consistent with previous findings that MTSET preferentially blocks WT-SCN5A channels with C373. Measurements were performed at 5 and 10 minutes after MTSET application to determine whether peak current density was measured at steady state. There were no significant differences in peak current density at 5 and 10 minutes after MTSET application, demonstrating that MTSET block reached its maximal effect after 5 minutes (data not shown). As expected, MTSET does not significantly decrease peak current densities in sodium channels with only the C373YSCN5A mutation (2 μg) (C373Y-SCN5A; FIG. 4B). Importantly, when WT-SCN5A channels (1 μg) are coexpressed in a 1:1 ratio with channels containing the C373Y-SCN5A mutation (1 μg), MTSET significantly decreased whole-cell sodium current by 42.6±9.5% (paired comparison, P=0.006) after 10 minutes (FIGS. 4A and 4B). This decrease in peak current density is due to the blockade of WT-SCN5A channels. Furthermore, MTSET blocked nearly all whole-cell sodium currents in cells expressing H558R-SCN5A alone (2 μg) by 90.6±11.7% ($P=3\times10^{-7}$) after 10 minutes (FIG. 4B). These data are further consistent with MTSET preferentially blocking functional sodium channels with a cysteine at amino acid residue 373.

We created a construct to produce hNav1.5 channels with both R282H and C373Y mutations (cis) on the same protein (R282H-C373Y-SCN5A). We hypothesized that if the H558R-SCN5A polymorphism rescues the R282H-SCN5A mutation by allowing the R282H-SCN5A mutant protein to traffic to the membrane, where it is functional, then MTSET should decrease peak sodium current density by 50% in cells coexpressing H558R-SCN5A and R282H-C373Y-SCN5A channels. MTSET significantly reduces whole-cell sodium current by 48.1±10.0% after 10 minutes (P=0.003; FIGS. 4A and 4B) in cells coexpressing H558R-SCN5A (1 μg) and R282H-C373Y-SCN5A channels (1 μg) (H558-RSCN5A+ R282H-C373Y-SCN5A). Furthermore, MTSET blocked nearly all current (reduction of 86±8%) in cells coexpressing 1 μg WT-SCN5A and 1 μg R282H-C373Y-SCN5A channels (WT-SCN5A/R282H-C373Y-SCN5A; FIG. 4B). These data demonstrate that hNav1.5 channels with the R282H-SCN5A mutation are functionally expressed in the plasma membrane in the presence of hNav1.5 channels with the H558R-SCN5A polymorphism but not in the presence of WT-SCN5A channels. MTSET eliminated only 50% of the currents when R282H-C373Y-SCN5A was coexpressed with H558R-SCN5A compared with almost all the currents when R282H-C373Y-SCN5A was coexpressed with WT-SCN5A. Therefore, MTSET predominantly blocked the H558R-SCN5A channels when coexpressed with R282H-C373Y-SCN5A channels because H558R-SCN5A channels maintain C373 in the protein sequence. The current remaining after application of 1 μmol/L MTSET was measured to determine the biophysical properties of the R282H-SCN5A mutated channel. The recovery and steady-state inactivation characteristics of the remaining R282H-C373Y-SCN5A channels were similar to control, suggesting that the R282H-SCN5A mutation is trafficking deficient but not functionally deficient in the membrane (Table 1).

Figure 5:
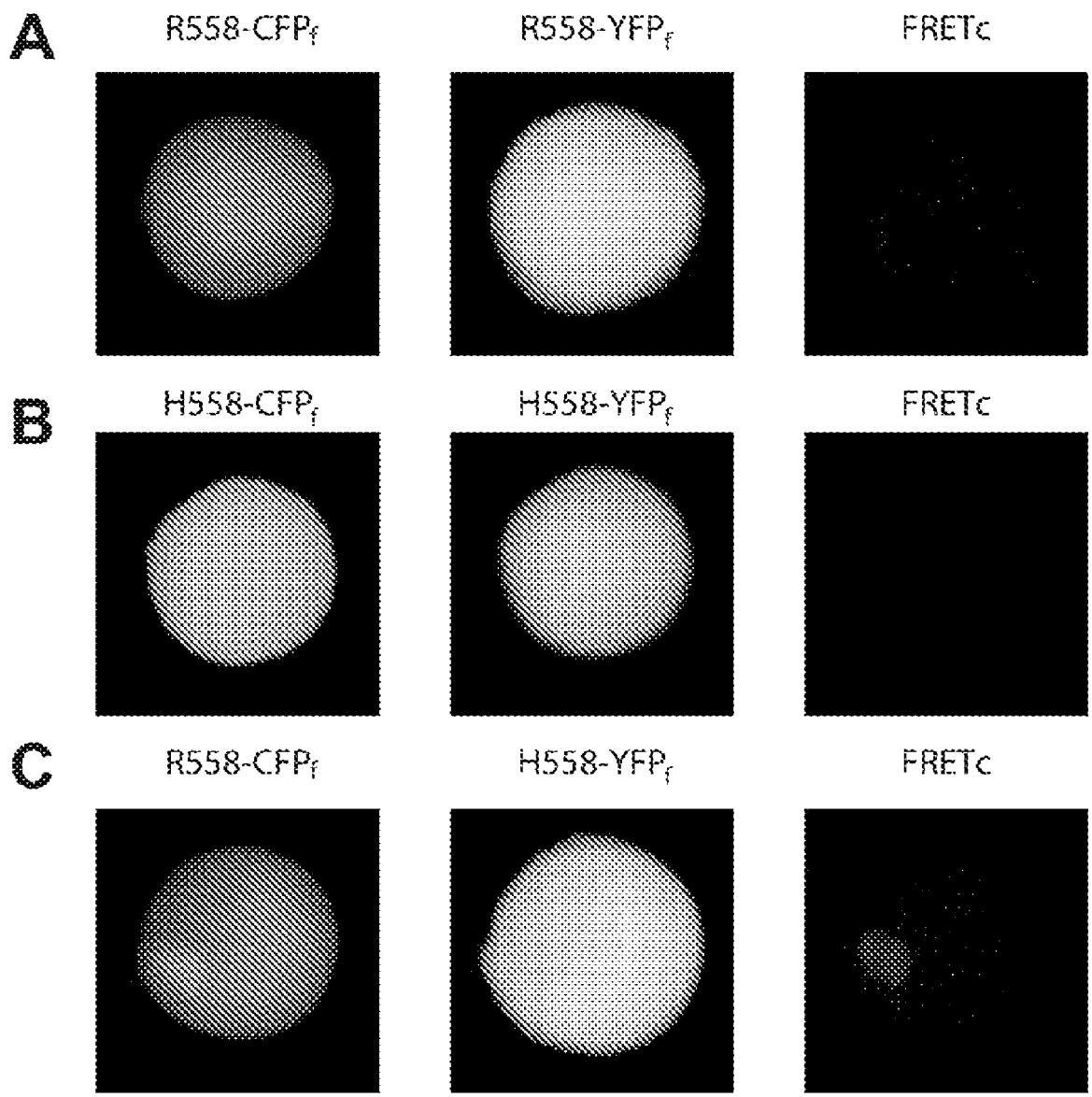
FIG. 5. Heterotypic fragments of hNav1.5 interact before protein trafficking to the cell membrane. A, When R558-CFPf (left) was coexpressed with R558-YFPf (center), little to no FRETc (right) occurred anywhere in the cells (n=33). B, Cells coexpressing H558-CFPf and H558-YFPf demonstrated little to no FRETc (n=24). C, Cells coexpressing R558-CFPf and H558-YFPf demonstrated FRETc within intracellular compartments only (n=34).

Mechanism of R282H-SCN5A Rescue by H558R-SCN5A: To determine whether the mechanism by which H558R-SCN5A rescues R282H-SCN5A is direct interaction of α-subunits, small hNav1.5 protein fragments centered on H558 fused to CFP or YFP were used for FRET studies. Three-channel FRET ratios were normalized to CFP and reported as FRETc as previously described by Vanderklish and colleagues, Proc Natl Acad Sci USA. 2000; 97:2253-2258. Representative FRET recordings are shown in FIG. 5. Fragments centered on 558 (40 amino acids) were fused to either CFP or YFP (FIG. 5). When cells coexpressed homotypic amino acid fragments (R558-CFP$_f$+R558-YFP$_f$ or H558-CFP$_f$+H558-YFP$_f$), there was little to no FRETc, as demonstrated in FIGS. 5A and 5B. Cells coexpressing R558-CFP$_f$+H558-YFP$_f$ had a 3-fold increase in FRETc values compared with the homotypic FRETc values specifically within internalized compartments of the cell (0.04±0.02 and 0.01±0.01, respectively; P=0.006; FIG. 5C). In all experiments, FRET was absent from the cell membrane, which is consistent with the inability of these protein fragments to traffic to the membrane. These data suggest that the interaction of the hNav1.5 protein first occurs within intracellular compartments of the cell before protein trafficking to the membrane. More importantly, hNav1.5 interaction occurs preferentially when 1 protein expresses R558 and the other expresses H558.

Discussion

Mutations of the SCN5A gene underlie multiple cardiac diseases such as the long-QT syndrome type 3 and BrS. Although the long-QT syndrome type 3 is most often associated with a gain in sodium channel function, BrS is associated with a loss of whole-cell sodium channel current and thereby manifests as a slow-conduction phenotype. Importantly, it is well documented that BrS is an autosomal dominant disease with variable penetrance. However, little is known of the mechanisms that underlie this variable penetrance. Baroudi et al., (*Circ Res.* 2002; 90:E11-E16) demonstrated that the individual BrS mutations R1232W-SCN5A and T1620M-SCN5A each produced functional sodium channels with biophysical properties significantly different from WT-SCN5A. However, the combination of the 2 mutations on the same gene (R1232WT1620M-SCN5A) blocked protein trafficking of the channel. Importantly, the Baroudi et al study offers a mechanism for explaining the severity of the disease but does not explain the mechanism of penetrance.

To the best of our knowledge, this is the first study to suggest that the penetrance of BrS can be explained by a polymorphism on an allele separate from that with the mutation. Furthermore, the mutation is fully rescued by a polymorphism. Importantly, instead of producing a loss of protein trafficking, this study suggests that the protein with the polymorphism restores the function of the mutant protein by interacting with the mutant before it traffics to the membrane.

The penetrance of BrS is better studied with larger multiplex families and calls into question whether the proposed mechanism is the only explanation for incomplete penetrance of the patient with the R282H-SCN5A mutation and the H558R-SCN5A polymorphism. Our in vitro studies strongly suggest that the H558R-SCN5A polymorphism restores the function of the R282H-SCN5A mutation and is consistent with the current phenotype of the asymptomatic patient (patient III-1) and her negative response to the flecainide challenge. Specifically, cells coexpressing equal amounts of R282H-SCN5A and H558R-SCN5A have peak current densities similar to an equal total amount of WT-SCN5A. When the concentration of H558R-SCN5A was reduced and coexpressed with an increased concentration of R282H-SCN5A, the peak current density was reduced, implying that the concentration of H558R-SCN5A is the limiting rescuing reagent. H558R-SCN5A also restores membrane trafficking of R282H-SCN5A-FLAG, as evidenced by confocal immunocytochemistry. Furthermore, we demonstrate that the R282H-C373Y-SCN5A mutation is rescued by H558R-SCN5A and that MTSET application reduces peak current density by 50% in cells transfected with equal amounts of R282H-C373Y-SCN5A+H558R-SCN5A. On the other hand, MTSET blocks almost all current in cells transfected with SCN5A that retains C373 and does not significantly change peak current with C373Y-SCN5A. This is strong evidence that the mutated channel is able to traffic to the membrane and produces a functional channel in the presence of the polymorphism.

The FRET data suggest that the domain 1 and 2 linker do not interact or have very weak interactions under normal conditions when 558 is a histidine in both proteins. Furthermore, the FRET studies potentially explain why WT-SCN5A channels do not rescue the R282H-SCN5A mutation because both mutant and WT channels express H558. Importantly, these data suggest that the degree of interaction between hNav1.5 subunits significantly increases when 1 protein encodes H558 and another encodes R558 (heterotypic proteins). However, the fact that WT-SCN5A (encoding H558) cannot rescue R282H-H558R-SCN5A suggests that the polymorphism must be on the nonmutated protein. One speculated mechanism of this rescue is that the H558R polymorphism needs to be on the nonmutated protein to help restore folding of the mutated channel, which will then allow it to traffic to the cell membrane.

Importantly, this study has many significant scientific implications. First, because of the incomplete penetrance nature of BrS, selective genotyping may not identify at-risk patients with 100% sensitivity without further consideration of complementary alleles. Second, heterotypic protein interaction may be a relatively unknown quality control mechanism. Furthermore, this study suggests that genetic polymorphisms may be a potential target for future therapies aimed at rescuing dysfunctional protein channels.

EXAMPLE 2

Effect of Peptides on Cells

Summary: Brugada Syndrome (BrS) is associated with mutations in the cardiac sodium channel (Na$_v$1.5) and presents risks of sudden cardiac death. Current treatments are not completely effective, can cause serious side effects, and do not address the underlying cause of the disease making it desirable to develop a gene therapy approach for treating BrS. We reported, in Example 1, that the function of a Na$_v$1.5 BrS mutation could be restored by co-expression with the common sodium channel polymorphism, H558R. Here, we hypothesize that peptide fragments from Na$_v$1.5, containing the polymorphism, H558R, can be used to restore trafficking and function of BrS mutations. Patch-clamping revealed that 40 and 20 amino acid fragments of Na$_v$1.5, containing the polymorphism restored function of mutant channels. Wild type peptides were not able to restore trafficking of the R282H channels. Fluorescence Resonance Energy Transfer suggested that the R282H mutation was misfolded and this was corrected upon co-expression with polymorphic peptides. Therefore, small peptides are sufficient to restore function of a BrS mutation, indicating that polymorphic peptides represent a viable option for use in a gene repair therapy approach to prevent BrS.

Introduction: The current treatment options for Brugada Syndrome are associated with complications and side effects that cause some patients to stop the therapy (as discussed before). Therefore, it is desirable to develop treatments that avoid the complications of ICD's and drug therapy, but also address the underlying causes of disease.

One alternative therapy that focuses on the genetic cause of the disease is gene therapy. Several laboratories are developing approaches to deliver specific genes to cardiac tissue to prevent arrhythmias. Kikuchi et al. and Sasano et al. described gene therapy approaches to deliver a mutant Human Ether-a-go-go-related Gene (hERG), using an adenoviral vector, to increase cardiac action potential duration and thereby prevent reentrant arrhythmias in the atria and border zone of the infarct, respectively. More recently, Kizana et al. found that delivering a mutant Connexin 43 gene decreased gap junctional intracellular communication and may help protect against ventricular tachycardia. Adeno-associated viruses (AAV's) have been shown to better target cardiac tissue and produce longer expression. T this approach requires the use of smaller construct. Therefore, a useful gene therapy approach for treating Brugada Syndrome would be one that uses only a fragment of a gene, which is sufficient to restore function of the mutant channel.

Gene fragments have shown potential for treating channelopathies. For example, a common mutation of the cystic fibrosis transmembrane conductance regulator (CFTR) can inhibit processing and trafficking of the channel, causing cystic fibrosis. Peptides have been used to make this channel exit the endoplasmic reticulum and translocate to the cell surface, thus restoring trafficking of the defective channel. Also, we know that some structural requirements for trafficking exist. For instance, coiled coil interactions have been described in the KCNQ1 and eag/erg families of potassium channels. Thus peptides that contain these structural elements would enhance trafficking and could be an avenue for gene therapy in diseases caused by channel trafficking defects. In fact, for the KCNQ1 and hERG potassium channels, small peptides from wild type channels have been used to restore trafficking to Long QT Syndrome mutations.

Mutations that cause an inability of the sodium channel to traffic to the cell membrane are the most common defect found to cause BrS. In Example 1, we demonstrated that the BrS-causing mutation R282H is an example of this type of mutation, which will render the channel unable to exit the endoplasmic reticulum and to traffic to the cell surface. We also identified a healthy individual with this BrS-causing mutation, R282H, on one allele and the common sodium channel polymorphism, H558R, on the other allele. We demonstrated that this individual did not have BrS because the polymorphic channel was able to restore trafficking of the mutant channel. We now hypothesize that a new gene repair therapy approach using peptide fragments of the cardiac sodium channel, containing the polymorphism, H558R, could be used to restore trafficking and function of the BrS mutation, R282H, by aiding in the folding of the channel. To examine this hypothesis, we first co-expressed the mutant channel with the polymorphic fragment in HEK-293 cells and used whole cell patch clamping to determine whether rescue occurred. We then employed Fluorescence Resonance Energy Transfer (FRET) to examine folding of the mutant channel in the absence and presence of the peptide.

Materials and Methods

Mutagenesis: The R282H mutation and H558R polymorphism were created on the $Na_v1.5$ background (PubMed Accession No. NM 198056) expressed in the GFP-IRES vector (BD Biosciences Clonetech, San Jose, Calif.) using the Stratagene QuikChange XL Site Directed Mutagenesis Kit.

Creation of Channel Fragments: Channel fragments were created by amplifying a small piece of either the wild type or the H558R polymorphic channel. These pieces were ligated into either the pcDNA3 vector or the pECFP-N3 vector (BD Biosciences Clonetech). The sequences for the fragments are: Wild Type 20 amino acid-NSTARESESHHTSLLVPWPL (SEQ ID NO: 10), Polymorphic 40 amino acid-GSEADFAD-DENSTAGESESHRTSLLVPWPLRRTSAQGQPS (SEQ ID NO: 4), and polymorphic 20 amino acid-NSTAGESESH RTSLLVPWPL (SEQ ID NO: 3).

Expression of $Na_v1.5$ and Fragments in HEK293 Cells: Transient transfection of $Na_v1.5$ and $Na_v1.5$ fragments into human embryonic kidney (HEK293) cells was accomplished using the Polyfect transfection kit (Qiagen, Valencia, Calif.) according to the manufacturer's protocol for 24 hours. When channels were expressed alone, 1 g of channel cDNA was used. For co-transfections, 1 µg of channel cDNA and 1 µg of fragment cDNA were combined.

Electrophysiology: Macroscopic sodium currents from transfected cells were recorded using the whole cell configuration of the patch clamp technique as previously described (Deschenes, I., et al., 2000 Cardiovasc. Res. 46: 55-65). Cells that emitted green fluorescence were considered successfully transfected. Patch electrodes were made from 1.5 mm thin walled glass capillaries (World Precision Instruments, Sarasota, Fla.). Low resistance electrodes (<2MΩ) were used, and a routine series resistance compensation of an Axopatch 200A was preformed to values >80% to minimize voltage clamp errors. Voltage clamp command pulses were generated by a microcomputer using PCLAMP software version 9.02 (Axon Instruments, Foster City, Calif.). To allow currents to stabilize, experiments were performed 10 minutes after entering whole cell configuration. Membrane currents were filtered at 5 kHZ and digitized with 12-bit resolution. The internal solution contained (in mmol/L) NaCl 35, CsF 105, EGTA 10, and Cs-HEPES 10 adjusted to pH7.4. The bath solution contained (in mmol/L) NaCl 140, KCl 5, $MgCl_2$ 1, $CaCl_2$ 2, HEPES 10, and glucose 10 adjusted to pH7.4. Experiments were performed at room temperature (22° C. to 23° C.).

Whole cell sodium current densities were measured by dividing the peak current obtained from stepping in 10 mV intervals from −80 to 30 mV from the holding potential of −120 mV by the cell capacitance. Cell capacitance was determined by integrating the area under the capacitive transient of a pulse from −80 mV to −70 mV. Time course of recovery from inactivation ($\tau_{rec}$) was studied using a 2-pulse protocol with a 30 ms prepulse to −30 mV with varying rest intervals at −120 mV, followed by a 30 ms test pulse to −30 mV (FIG. 7C inset). Peak current amplitude was fit to the following equation:

$$I_{test}/I_{pre-pulse}=1-\exp(-t/\tau_{rec})$$

Voltage dependence of steady state inactivation was determined by 500 ms prepulses ranging from −140 to −30 mV (FIG. 7B inset). Peak current was fit to a Boltzmann distribution:

$$I/I_{max}=(1+\exp[(V-V_{1/2})/k_v])^{-1}$$

Conductance was calculated from peak current obtained by holding the resting membrane potential at −120 mV and stepping in 10 mV intervals from −80 mV to 20 mV according to the equation:

$$G=I/(V_{m-Vrec})$$

The conductance was also fit to a Boltzmann distribution. Time constant of inactivation was measured by fitting individual current traces from the peak current to the end of the pulse with a single exponential:

$$I(t)=A^*\exp(-t/\tau)$$

The persistent current was measured using a 300-ms pulse to −30 mV. Tetrodotoxin (TTX, Sigma, St-Louis, Mo.) blocked current averaged between 280 and 300 ms was subtracted from the current before drug and expressed as a percentage of peak current.

Image Analysis and Calculation of Fluorescence Resonance Energy Transfer Ratios: Images were acquired with and Olympus IX71 fluorescent microscope that was fitted with a Hamamatsu ORCA-ER charge coupled device (12 bit)

and controlled by the SLIDEBOOK software package from Intelligent Imaging Innovations (Denver, Colo.). Filter cube specifications for the fluorescent channels were as follows for excitation and emission, respectively: enhanced cyan fluorescent protein (CFP), 430±25 and 470±30 nm; enhanced yellow fluorescent protein (YFP), 500±20 and 535±30 nm, and fluorescence resonance energy transfer (FRET), 430±25 and 535±30 nm.

Image analysis involved three basic operations: subtraction of background autofluorescence and blurred light, quantification of fluorescence intensity, and calculation of a corrected FRET (FRETc) using the following equation:

$$FRETc = (I_{DA} - aI_{AA} - dI_{DD})/I_{DD},$$

Where $I_{DA}$ is the fluorescence intensity of the cell measured from the FRET filter set and $I_{DD}$ and $I_{AA}$ are the fluorescent intensities of the same cell measured from the CFP (donor) and YFP (acceptor) filter sets, respectively. The cross-talk coefficients, a and d, are considered constant and a property of our microscope's filter sets, with a=0.03 and d=0.63. The corrected FRET ratio (FRETc) includes normalization to $I_{DD}$ to correct for variances in protein expression from cell to cell.

FRET Constructs: The FRET construct was created using a transposon approach, which randomly inserts the gene from the transposon construct into the $Na_v1.5$ construct. The p(AmpR)R6Kyori transposon (Epicenter Technologies) was altered to contain the Enhanced Yellow Fluorescent Protein (YFP) upstream of the Ampicillin gene. Through mutagenesis, restriction sites were created on each end of the Amp gene to facilitate later removal. The newly formed YFP-transposon was then transposed into the pre-existing $Na_v1.5$ vector with Kanamycin resistance and with CFP fused to the C-terminal region of the sodium channel. The double antibiotic resistance, Amp/Kan, was used to select for transposed clones. Diagnostic digests followed by sequencing were used to ensure that the YFP inserted in the sodium channel gene in the correct orientation and frame and to identify the location of insertion. Removal of the Amp gene from correctly transposed clones was accomplished by digestion with engineered restriction sites. The construct containing YFP inserted at position 1022 was used because it produced significant FRET measurement and functional sodium currents. Mutagenesis was done on this construct to insert the R282H BrS mutation.

The positive control used for the FRET experiment was a CFP-YFP dimer, in which CFP and YFP were linked by a short amino acid chain. The negative FRET control was CFP and YFP co-expressed in HEK293 cells on separate vectors, pECFP-C1 and pEYFP-N1 (BD Biosciences Clonetech, San Jose, Calif.).

Statistical Analysis: Statistical analysis of the data was performed with a single factor ANOVA and a post hoc, 2-sided, Dunnett's test, using the statistical program SPSS (SPSS Inc. Chicago, Ill.). The Dunnett's test compares each sample to control. In this study, the control was currents produced from wild type (WT) channels. A value of p<0.05 was considered statistically significant. All data is reported as mean ±SE.

Results

Polymorphic Peptides Restore Trafficking of R282H Mutant Channels: To determine if channel fragments were capable of restoring trafficking of the BrS mutant channel, whole cell sodium currents were recorded from HEK293 cells co-expressing the R282H mutant channel and fragments of either wild type or polymorphic cardiac sodium channels.

Representative current traces elicited from transfected cells are shown in FIG. 6A. Cells expressing R282H alone lacked whole cell sodium current, in line with previous reports that this mutation produces a trafficking deficient channel. On the other hand, when the mutant channel was co-transfected with a 40 amino acid channel fragment containing the H558R polymorphism, R282H+R558-40aa, whole cell current was increased to 30% of wild type level. Furthermore, co-expression with a 20 amino acid polymorphic fragment, R282H+R558-20aa, further increased current density (FIG. 6B) to 75% of the wild type level. In addition, when WT channels were co-expressed with the 40 amino acid fragment, WT+40-aa, the current density was not significantly different from WT channels alone (−474.1±125.9 pA/pF vs. −337.7±105.8 pA/pF). These results indicate that a small polymorphic peptide is able to specifically restore trafficking of the mutant channel.

Figure 6:
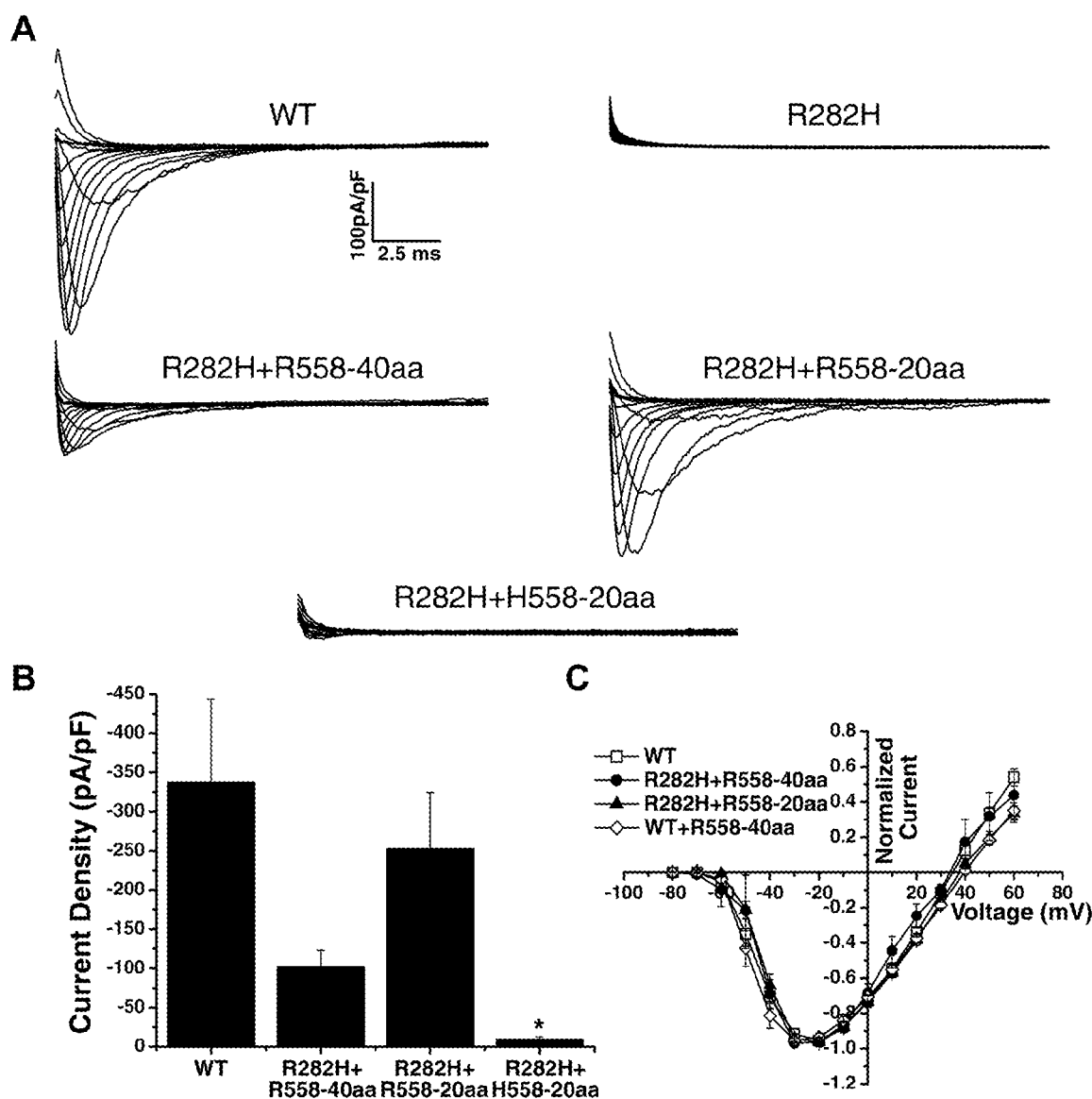
FIG. 6: Polymorphic Peptides Restore Function of the R282H Sodium Channel Mutant A. Whole cell sodium current traces recorded from transfected HEK293 cells. The R282H mutation expressed alone does not produce any current. Current was restored when the mutant was co-expressed with polymorphic peptide treatment (R282H+R558-40aa and R282H+R558-20aa), but not when co-expressed with the WT peptide (R282H+H558-20aa). B. Peak sodium current densities. Current density was similar for WT (n=6), R282H+R558-40aa (n=8), and R282H+R558-20aa (n=12) and significantly lower for R282H+H558-20aa (n=11). C. Current-Voltage Relationships were similar for all conditions. *p<0.05 compared to WT.

To ascertain that the polymorphism was necessary for rescue, the mutant channel was co-expressed with the corresponding 20 amino acid fragment of the wild type channel, R282H+H558-20a (FIG. 6). In this condition, restoration of current was not observed, indicating that the polymorphism is required to restore trafficking of the R282H mutant.

Biophysical Properties of Rescued Currents: Having shown that polymorphic peptides were capable of restoring trafficking of the R282H mutant channel, we next compared the biophysical properties of rescued currents to wild type (WT) currents. To establish whether differences were a consequence of the mutant channel's phenotype or a non-specific effect of the peptide, WT channels were co-expressed with the polymorphic peptide, R558-40aa. The current voltage relationship, activation curve, voltage dependence of steady state inactivation, recovery from inactivation, time constant of inactivation, and persistent current were measured for wild type (open symbols) and rescued R282H currents (closed symbols). We found that the current voltage relationship (FIG. 6C) is not different between rescued and wild type currents. The activation curve (FIG. 7A) for rescued currents was also similar to wild type. However, rescued R282H currents differed from WT currents in steady state inactivation, which was shifted to more depolarized voltages, and recovery from inactivation was faster, compared to wild type (FIGS. 7B-C and Table 2). Since the channel appeared to have impaired inactivation, we also measured the level of TTX-sensitive persistent current at the end of 300-ms depolarizing pulse for the rescued R282H currents. These experiments demonstrated a significant increase in the level of persistent current (R282H: 0.37±0.08% n=7 vs WT: 0.15±0.07% n=5). Finally, the time course of inactivation (FIG. 7D) was slower for channels rescued with the peptides, but only reached significance for channels treated with the smaller 20 amino acid peptide.

Figure 7:
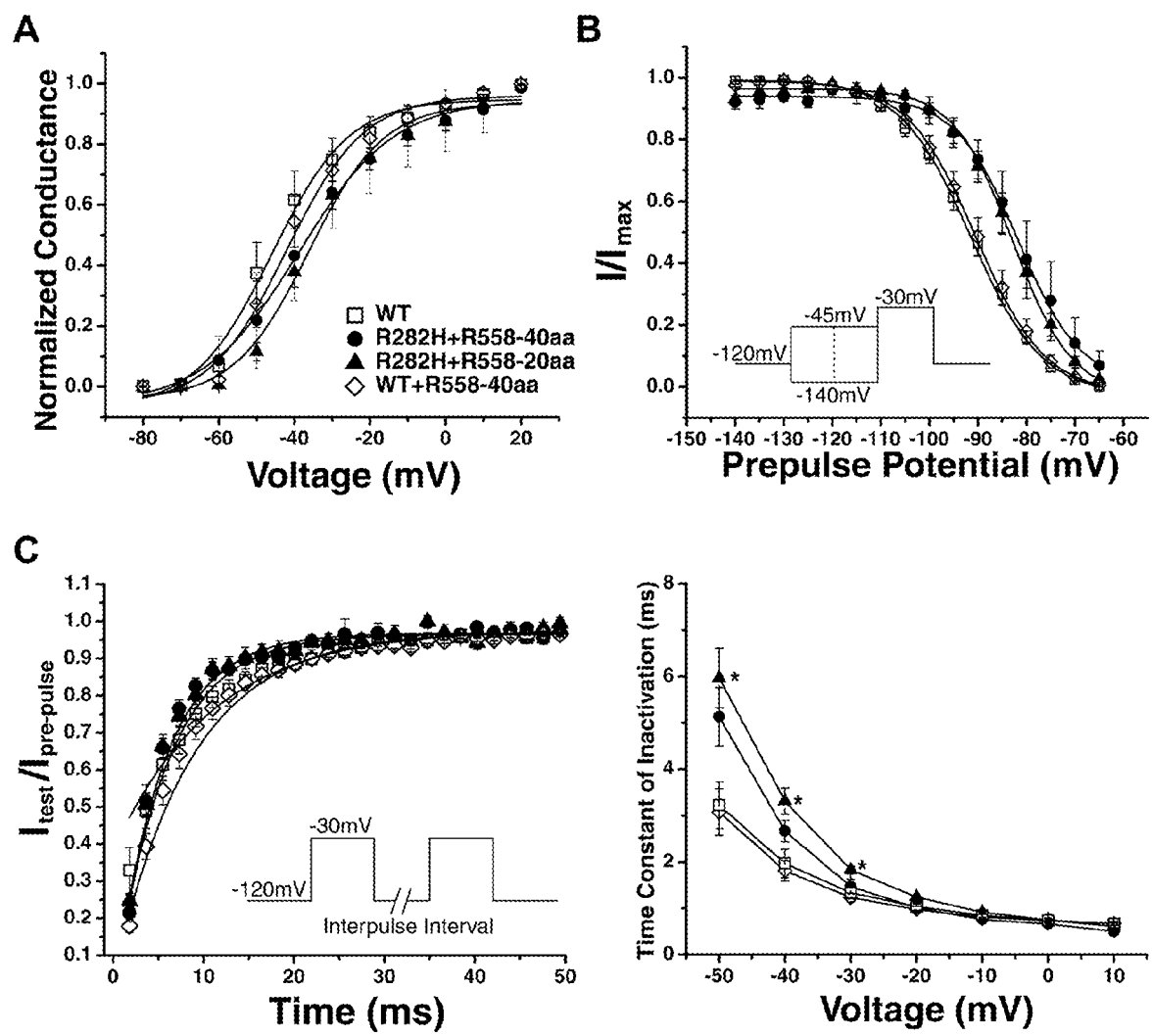
FIG. 7: Biophysical Properties of Rescued Currents are Altered A. Conductance was similar for WT, rescued channels (R282H+R558-40aa and R282H+R558-20aa), and WT channels treated with the polymorphic peptide (WT+R558-40aa). B. Steady Sate-Inactivation of rescued currents (closed symbols) was significantly shifted toward more depolarized potentials. C. Recovery from Inactivation. The time constants of recovery from inactivation were significantly faster for rescued channels compared to WT. D. Time Constant of Inactivation. Inactivation of R282H+R558-20aa channels (n=9) was significantly slower than WT channels (n=7). R282H+R558-40aa channels (n=5) and WT+R558-40aa channels (n=9) behaved similarly to WT. *p<0.05 compared to WT.

Importantly, none of these differences were observed when wild type channels were treated with the polymorphic peptide, WT+R558-40aa (FIG. 7). Taken together, the biophysical data suggests that the rescued R282H channels express a mutant phenotype dominated by impaired inactivation, and that the fragments do not affect biophysical properties of WT channels.

TABLE 1

Conductance, Steady State Inactivation, and Recovery from Inactivation Parameters for Whole Cell Sodium Currents

| Channel | Conductance $(V_{1/2})$, mV | Steady State Inactivation $(V_{1/2})$, mV | Recovery from Inactivaion $(\tau_{rec})$, ms |
|---|---|---|---|
| WT | −43.8 ± 3.7 | −91.9 ± 1.7 | 8.4 ± 1.0 |
| R282H+R558-40aa | −40.8 ± 5.1 | −80.6 ± 2.7* | 4.5 ± 0.4* |

TABLE 1-continued

Conductance, Steady State Inactivation, and Recovery from
Inactivation Parameters for Whole Cell Sodium Currents

| Channel | Conductance ($V_{1/2}$), mV | Steady State Inactivation ($V_{1/2}$), mV | Recovery from Inactivaion ($\tau_{rec}$), ms |
|---|---|---|---|
| R282H+R558-20aa | −36.8 ± 1.6 | −82.8 ± 1.5* | 5.0 ± 0.5* |
| WT+R558-40aa | −40.2 ± 3.3 | −90.0 ± 1.6 | 7.0 ± 0.7 |

Rescued currents differ from WT in Steady State Inactivation and Recovery from Inactivation
*p < 0.05 compared to WT R282H Affects Channel Structure: We demonstrated in Example 1 that the absence of current observed with the R282H mutation is due to a trafficking defect. A common cause of trafficking deficient channels is misfolding of the protein which does not allow the channel to exit the endoplasmic reticulum and traffic to the cell membrane. One possible mechanism by which the polymorphic peptide may rescue the R282H mutant is by restoring proper folding of the mutated channel. Fluorescence Resonance Energy Transfer (FRET) was used to examine folding of the trafficking deficient mutant channel, R282H, in the presence and absence of the polymorphic peptide. To accomplish this, a sodium channel construct containing a pair of fluorescent proteins capable of transferring energy from one to the other was created, using a transposon approach.

Figure 8:
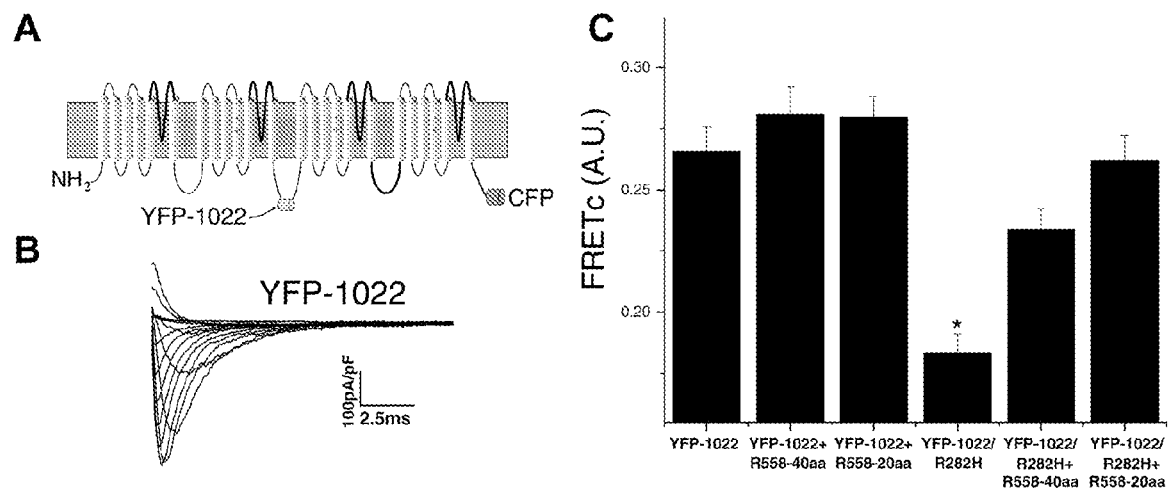
FIG. 8: FRET in Normal and Mutant Channels A. Diagram of FRET construct containing CFP fused to the C-terminus of hNav1.5 and YFP inserted into the Domain II-III linker at amino acid position 1022. B. Currents elicited from the FRET construct are similar to WT currents. C. FRETc values for YFP-1022 (n=43) were similar to YFP-1022+R558-40aa (n=35), YFP-1022+R558-20aa (n=39), YFP-1022/R282H+R558-40aa (n=43), YFP-1022/R282H+R558-20aa (n=46). FRETc of YFP-1022/R282H (n=45) alone was significantly smaller than WT. *p<0.05 compared to WT.

The cardiac sodium channel used for these experiments, YFP-1022, had Enhanced Cyan Fluorescent Protein (CFP) fused to the C-terminus of the channel and Enhanced Yellow Fluorescent Protein (YFP) inserted into the Domain II-III linker at amino acid position 1022 (FIG. 8A). This construct produced functional channels, as demonstrated by their ability to conduct sodium current (FIG. 8B). YFP-1022 was associated with a corrected FRET (FRETc) value of 0.27±0.01 as shown in FIG. 8C. This value was significantly greater than the negative control (0.16±0.01 p<0.001). When the R282H mutation was created on YFP-1022 (YFP-1022/R282H), the FRETc value decreased significantly, to 0.18±0.01 but was still significantly different from negative control (p=0.02). The FRET decrease indicated that the 3-D structure of the channel has changed so that the YFP and CFP were now further apart. This is likely due to the fact that the R282H mutant channel is improperly folded. Interestingly, when fragments containing the polymorphism were co-expressed with the YFP-1022/R282H construct, FRETc was restored to values similar to the non-mutated YFP-1022 (FIG. 8C), which may indicate that the mutated channel YFP-1022/R282H has now obtained a conformation similar to that of the functional YFP-1022 channel, which likely explains the ability of the mutant channel to traffic in presence of the polymorphic peptide. Similarly, when the YFP-1022/R282H construct was expressed in presence of the drug mexilitine which is known to restore trafficking of the R282H mutant, FRETc values were also restored to the level of the non-mutated YFP-1022 (data not shown). This supports the hypothesis that the mutant channel, either in presence of the drug or with the polymorphic peptide, is now folding properly, which allows the channel to traffic to the cell membrane and to produce currents.

To exclude non-specific effects of the peptide, non-mutated YFP-1022 channels were co-expressed with polymorphic fragments. No FRETc increase was observed in these cells (FIG. 8C), confirming that the increase in FRETc seen when YFP-1022/R282H is co-expressed with the polymorphic peptide is specific.

Discussion

Brugada Syndrome is associated with mutations in the cardiac sodium channel that decreases whole cell sodium currents, often by reducing channel expression at the cell surface. This lack of whole cell sodium current causes an increased risk of sudden cardiac death in patients with BrS. Treatment strategies, including ICD implantation, are generally aimed at terminating episodes of arrhythmia, but without decreasing the patient's likelihood of having an arrhythmic event. Furthermore, these therapies for BrS are not entirely effective at terminating arrhythmias and carry a high risk of complications. Thus, it is desirable to develop an approach that could treat BrS by restoring trafficking to mutant sodium channels without harming WT. Through gene therapy, such a goal could be accomplished by delivering a gene that restores trafficking to deficient channels.

Another puzzling aspect of BrS is its incomplete penetrance. If we understood the mechanisms that underlie how a person with a disease causing mutation is able to show no symptoms of the disease, perhaps these mechanisms could be incorporated into a treatment for BrS. The presence of polymorphisms may contribute to penetrance and severity of some forms of congenital heart diseases. One study found that the presence of the R1193Q polymorphism attenuated the symptoms of one patient's inherited cardiac conduction defect. In Example 1, we went even further by demonstrating that incomplete penetrance could be explained by the presence of a common sodium channel polymorphism, H558R. Therefore, our approach was to learn from polymorphisms that affect the behavior of channels and apply these mechanisms as a gene therapy that would correct the defect of the mutant gene. In this paper, we address both the mechanism of H558R's rescue of R282H and the feasibility of using this polymorphism in a gene repair therapy approach for treating BrS.

It is commonly thought that channels which fail to traffic to the cellular membrane are misfolded, but very little work has been done to examine this popular theory. Studying the structure and folding of the sodium channel presents a unique challenge because of the channel's large size and lack of a crystal structure. So we employed a FRET based approach to study folding of the channel. FRET has been used to study the interactions between subunits of channels and movements within a channel, but to the best of our knowledge has not been used to study folding in the presence of a mutation. When R282H was introduced in a functional channel construct, containing CFP and YFP, the folding of the channel became altered, as shown by the decrease in FRETc signal and confirmed by the absence of current with the R282H mutation. In Example 1, we showed that this mutant channel is retained in the ER, and it appears that altered folding may be the cause of ER retention. In the presence of either size polymorphic peptide, folding, as indicated by the restored FRETc value, was corrected. This data suggests that in the presence of the polymorphic fragment, the mutant channel is able to fold properly. This indicates that the mechanism by which the polymorphism rescues the mutant channel involves either directly assisting in channel folding or allowing another protein to interact with the channel to correct folding.

This report is the first to present a new alternative strategy for treating BrS that for the first time addresses the underlying cause of the disease by restoring the function of the defective gene. Additionally, this new gene repair approach has the advantage of using only a small fragment of the target gene which should reduce the problems usually seen with gene therapy when an entire gene is transferred. Therefore, polymorphic peptides represent currently the most promising option to treat Brugada Syndrome.

EXAMPLE 3-10

Amino Acid Polymorphic Peptide Restores Function of the R282H Sodium Channel Mutant We repeated the above study with a 10 amino acid peptide having the sequence: ESHRTSLLVP (SEQ ID NO: 9).

The materials and methods were the same as for the 20 and 40 amino acid peptides, described above.

Figure 9:
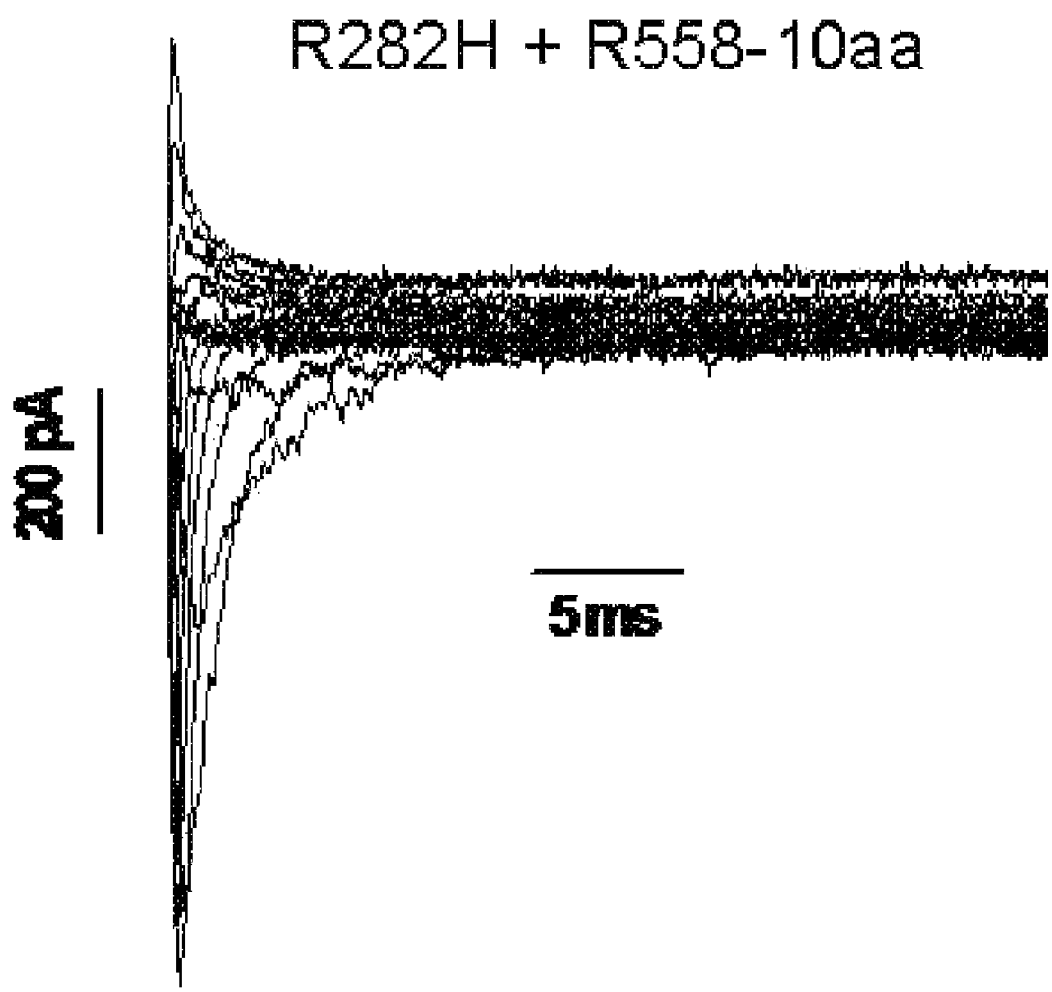
FIG. 9: 10 Amino Acid Polymorphic Peptide Restores Function of the R282H Sodium Channel Mutant. Whole cell sodium current traces recorded from transfected HEK293 cells. The R282H mutation expressed alone does not produce any current. Current was restored when the mutant was co-expressed with polymorphic peptide treatment (R282H+R558-10aa).

Results: Cells expressing the R282H Brugada Syndrome mutation alone lack whole cell sodium current (FIG. 9), in line with previous reports that this mutation produces a trafficking deficient channel. However, when the mutant channel was co-transfected with a 10 amino acid channel fragment containing the H558R polymorphism, R282H+R558-10aa, whole cell current was increased to 70% of wild type level. These results indicate that a small polymorphic peptide of 10 amino acids is able to specifically restore trafficking of the mutant channel.

EXAMPLE 4

SCN5A Polymorphism Decreases Arrhythmogenic Events in a Family Carrying a LQT3 Mutation Defects in the cardiac sodium channel gene, SCN5A, can cause Long QT3 syndrome (LQT3). A family which exhibited an atypical LQT3 phenotype was genotyped.

Figure 10:
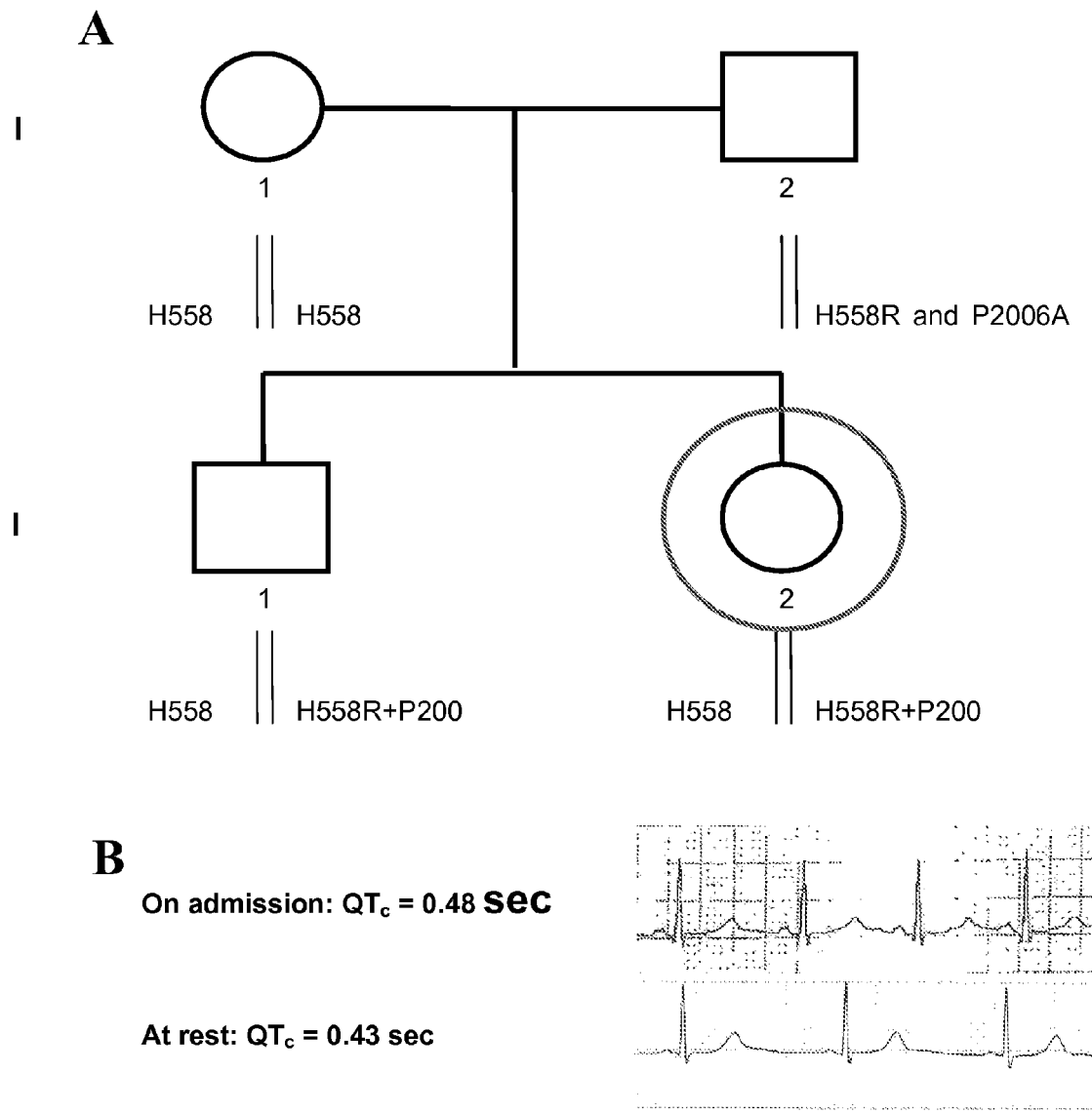
FIG. 10: Pedigree of a family with LQT3. II-1 is asymptomatic and II-2 had several syncope episodes. Both II-1 and II-2 do not show the typical LQT ECG pattern at rest despite having the SCN5A-P2006A mutation. They are homozygous for the sodium channel polymorphism H558R.

A 17 year old girl member of the family presented with episodes of syncope. However, she did not present with a prolonged QT interval but after genotyping we found that she carries a LQT3 mutation along with a common sodium channel polymorphism (FIG. 10A). The SCN5A-P2006A mutation was found. Additionally, the patient was found to be homozygous for the sodium channel polymorphism H558R. Her family was also genotyped and her brother and father were found to also carry the LQT3 mutation P2006A along with the H558R polymorphism. Neither of them had ever exhibited LQT events of syncope and their QT intervals were also normal.

Therefore, based on the unusual LQT3 phenotype that the patients and her family exhibited, we hypothesized that the H558R-SCN5A polymorphism could modify gating kinetics in mutated sodium channels. All methods used in this study were as described above in Examples 1 and 2.

Figure 11:
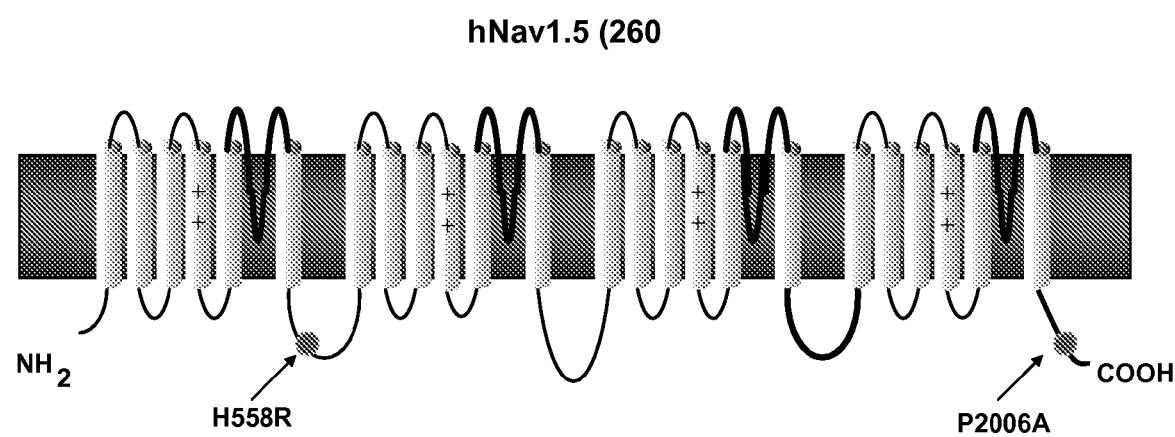
FIG. 11. Cartoon illustrating the hNaV1.5. Red circles represent amino acid residues where mutations and/or polymorphism occur.

Using site directed mutagenesis, we introduced the P2006A mutation, and the H558R polymorphism on the cardiac Na channel (FIG. 11) as described above. We then transiently transfected HEK-293 cells with recombinant: WT-SCN5A; P2006A-SCN5A; and (P2006A+H558R)-SCN5A. Whole-cell sodium currents were measured in HEK-293 cells using the patch clamp technique at room temperature.

Figure 12:
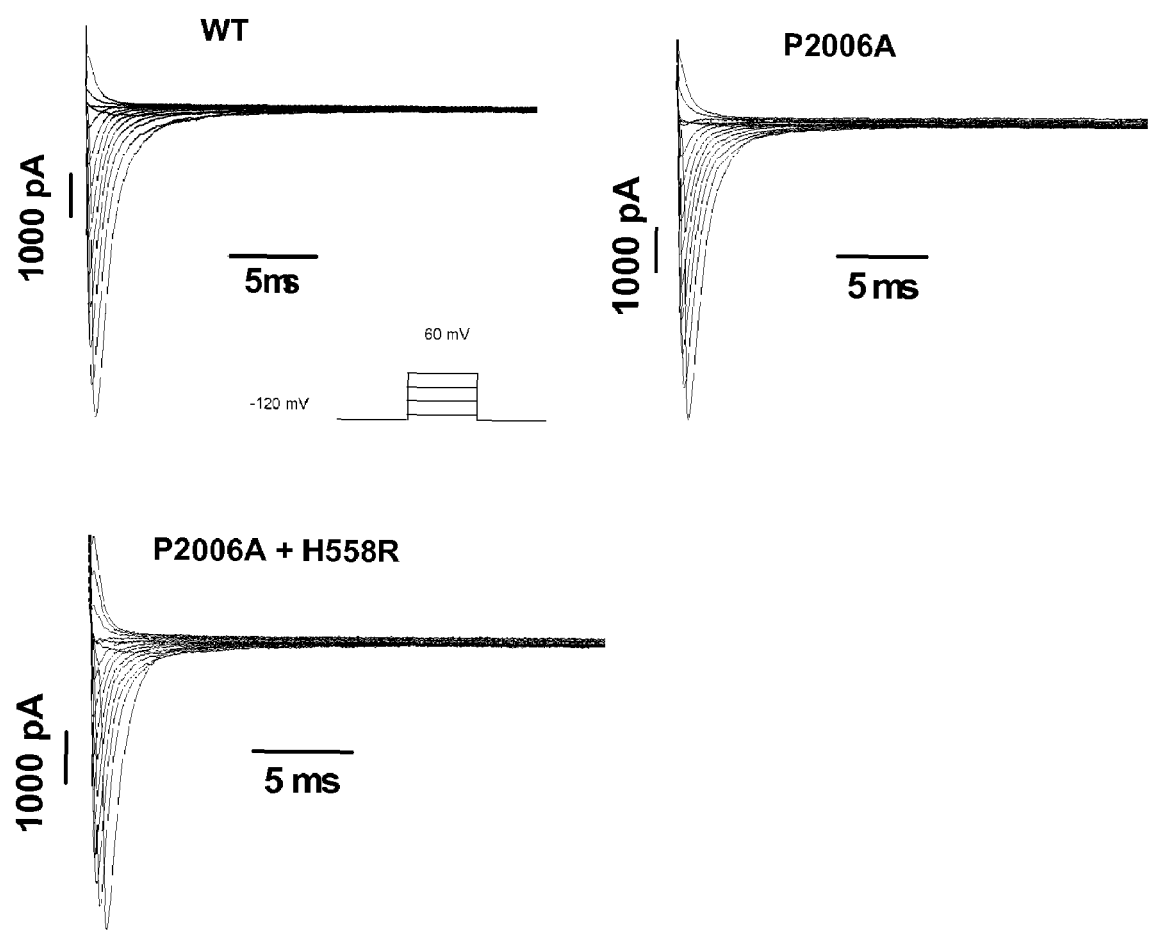
FIG. 12. Sodium currents recorded from P2006A mutation and P2006A+H558R were similar to currents recorded from the wild-type cardiac sodium channel (hNav1.5).
Figure 13:
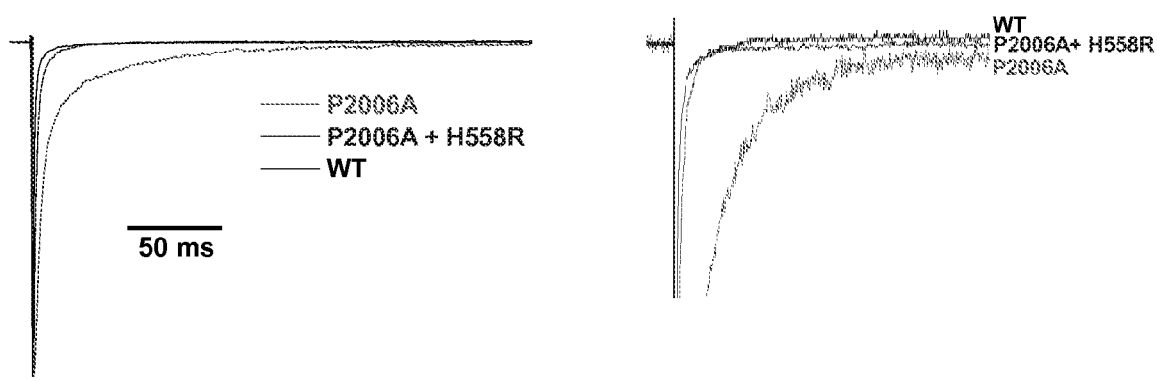
FIG. 13: TTX-sensitive persistent sodium currents for WT-SCN5A (black), SCN5A-P2006A mutation (red), and SCN5A-P2006A mutation with the sodium channel polymorphism H558R (blue).
Figure 14:
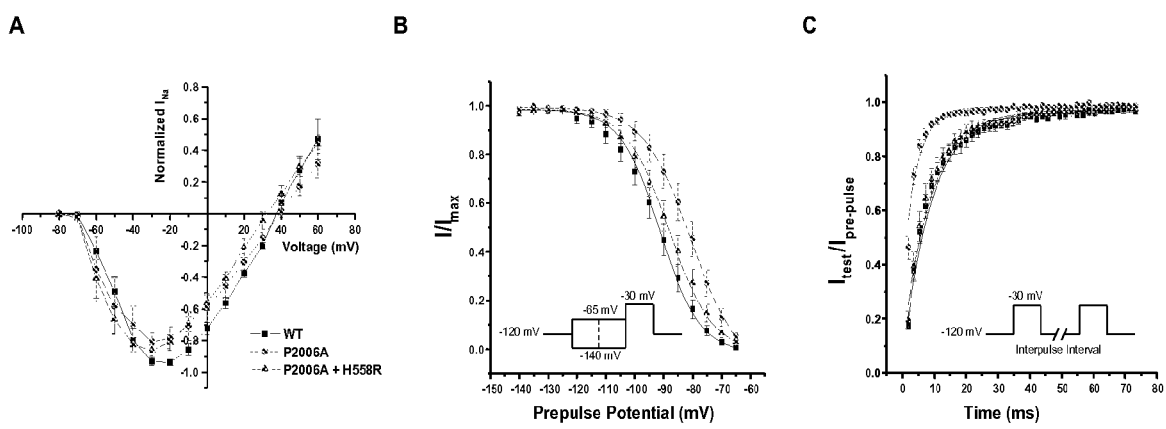
FIG. 14: Electrophysiological characterization of the P2006A mutation and P2006A+H558R in which currents were observed show biophysical properties comparable to wild-type channels for P2006A+H558R. However the inactivation state was destabilized for the P2006A mutation. A. I/V relationship B. Steady-State Inactivation C. Recovery from Inactivation.

P2006A exhibited significantly increased persistent sodium currents. P2006A also displayed significant depolarizing shifts in voltage dependence of inactivation and faster recovery from inactivation. Interestingly, when the mutation was expressed in the presence of the H558R polymorphism, the sodium currents behaved like WT. Interestingly, the H558R polymorphism can modify the gating kinetics in this mutation which may explain the atypical LQT3 phenotype seen in the patients that carry both a mutation and a polymorphism. These observations may provide a plausible mechanism for decreased arrhythmogenic events in LQT3 patients that also carry a polymorphism as is the case of this family. FIG. 12 shows odium currents recorded from P2006A mutation and P2006A+H558R were similar to currents recorded from the wild-type cardiac sodium channel (hNav1.5). FIG. 13 shows TTX-sensitive persistent sodium currents for WT-SCN5A (black), SCN5A-P2006A mutation (red), and SCN5A-P2006A mutation with the sodium channel polymorphism H558R (blue). FIG. 14 shows the electrophysiological characterization of the P2006A mutation and P2006A+H558R in which currents were observed to show biophysical properties comparable to wild-type channels for P2006A+H558R. However the inactivation state was destabilized for the P2006A mutation.

TABLE 3

Persistent current, recovery from inactivation, and steady-state inactivation parameters of whole-cell sodium current.

| | WT (n = 12) | P2006A (n = 12) | P2006A +H558R (n = 20) |
|---|---|---|---|
| Persistent Current | 0.15% | 1.20%* | 0.30% |
| Recovery from Inactivation (ms) | 8.9 ± 0.4 | 4.4 ± 0.3* | 8.8 ± 0.4 |
| Steady-State Inactivation (mV) | −91.2 ± 0.8 | −80.6 ± 1.8* | −88.1 ± 1.0 |

This work can guide cardiologists in selecting a therapeutic approach for asymptomatic family members of patients with inherited life-threatening arrhythmias. This work will also assist in helping select patients who are most likely to benefit from an expensive and risky therapy, the implanted defibrillator (ICD). Additionally, genetic polymorphisms are a potential target for future therapies aimed at rescuing dysfunctional protein channels.

EXAMPLE 5

Treatment of Heart Failure

Recent studies suggest that the failing heart is not refractory to treatment, as was previously believed. For example, the observation that a small percentage of subjects with left ventricular assist devices (LVADs) can be permanently weaned from their device strongly suggests that damaged hearts are capable of recovering lost function.

A group of investigators recently assessed the effect of SCN5A H558R polymorphism on mortality in a group of patients with systolic heart failure. (Aleong et al. 2005, The cardiac sodium channel H558R variant improves survival in heart failure, *Heart Rhythm* 2005; 2:S104-05). They found that the R allele of the SCN5A H558R polymorphism predicts improved survival in heart failure patients. This result is similar to our findings for the Brugada syndrome and LQT3 diseases discussed above. Therefore, the invention contemplates methods of treating subjects who have been diagnosed as having heart failure by administering to the subjects a therapeutically effective amount of the peptides as described above.

The invention claimed is:

1. An isolated peptide that is from 10 to 100 amino acids in length, wherein the peptide comprises a sequence that is 100% identical to all or a portion of SEQ ID NO: 2, wherein said portion comprises the sequence SESHIRTSLLV (SEQ ID NO: 1).

2. The isolated peptide of claim 1, wherein said peptide has the sequence SEQ ID NO: 1, 2, 3 or 4.

3. The isolated peptide of claim 2, wherein said peptide has the sequence SEQ ID NO: 1.

4. The isolated peptide of claim 2, wherein said peptide has the sequence SEQ ID NO: 2.

5. The isolated peptide of claim 2, wherein said peptide has the sequence SEQ ID NO: 3.

6. The isolated peptide of claim 2, wherein said peptide has the sequence SEQ ID NO: 4.

7. An isolated peptide comprising the sequence SEQ ID NO: 9.

8. A method of treating a subject that has a genetic predisposition to, or has been diagnosed as having, a cardiac disorder related to dysfunctional SCN5A sodium channels, comprising administering to the subject a therapeutically effective amount of a peptide that is from 10 to 100 amino acids in length wherein the peptide comprises a sequence that is 100% identical to all or a portion of SEQ ID NO: 2, wherein said portion comprises the sequence SESHRTSLLV (SEQ ID NO: 1).

9. The method of claim 8, wherein the peptide has the sequence SEQ ID NO: 1, 2, 3, or 4.

10. The method of claim 8, wherein the cardiac disorder is Brugada's syndrome, Long QT3 syndrome or heart failure.

* * * * *